(12) United States Patent
Zhou

(10) Patent No.: US 11,397,562 B2
(45) Date of Patent: Jul. 26, 2022

(54) SYSTEM AND METHOD TO GENERATE SOFTWARE DEVELOPMENT AND TESTING STORIES UTILIZING MULTI-DIMENSIONAL KNOWLEDGEBASE (MDK)

(71) Applicant: Yingshu Zhou, Victoria, MN (US)

(72) Inventor: Yingshu Zhou, Victoria, MN (US)

( * ) Notice: Subject to any disclaimer, the term of this patent is extended or adjusted under 35 U.S.C. 154(b) by 0 days.

(21) Appl. No.: 17/068,478

(22) Filed: Oct. 12, 2020

(65) Prior Publication Data
US 2021/0109715 A1 Apr. 15, 2021

Related U.S. Application Data

(60) Provisional application No. 62/915,112, filed on Oct. 15, 2019.

(51) Int. Cl.
*G06F 8/10* (2018.01)
*G06F 8/20* (2018.01)

(52) U.S. Cl.
CPC . *G06F 8/10* (2013.01); *G06F 8/20* (2013.01)

(58) Field of Classification Search
CPC .................................................. G06F 8/10–20
USPC ............................... 717/102–121; 706/45–50
See application file for complete search history.

(56) References Cited

U.S. PATENT DOCUMENTS

| | | | | |
|---|---|---|---|---|
| 6,144,954 A * | 11/2000 | Li | .................. | G05B 19/0426 |
| | | | | 706/62 |
| 6,675,164 B2 * | 1/2004 | Kamath | .............. | G06F 16/2465 |
| | | | | 706/45 |
| 6,782,511 B1 * | 8/2004 | Frank | .................. | G06F 30/327 |
| | | | | 716/108 |
| 7,065,512 B1 * | 6/2006 | Bertrand | .................. | G09B 7/02 |
| | | | | 706/14 |
| 7,113,956 B1 * | 9/2006 | Elias | ...................... | G06N 5/022 |
| 7,130,807 B1 * | 10/2006 | Mikurak | ............ | G06Q 30/0202 |
| | | | | 705/7.31 |

(Continued)

OTHER PUBLICATIONS

Bruckmann et al., "AMABULO—A Model Architecture for Business Logic", IEEE, pp. 445-452 (Year: 2008).*

(Continued)

*Primary Examiner* — Anil Khatri

(57) ABSTRACT

A system to generate software development and testing stories that includes a design specification system, a collection module, identification module, creation module, selection module, analysis module, development module, and a feeding module. The design specification system contains software design data. The collection module collects software design data. The identification module identifies Base Software Business Logic Paths (BSBLP). The identification module also identifies the base factors, non-base factors, and values of the base factors, and non-base factors for each BSBLP. The creation module places the base factors, non-base factors, and the values inside an Initial Factor List (IFL) to build Multi-Dimensional Knowledgebases (MDK). The selection module selects relevant BSBLP for a subject software feature to be analyzed. The analysis module utilizes the relevant BSBLP to perform factor impact analysis on the subject software feature to develop a Final Factor List (FFL). The development module generates the software development and testing stories.

16 Claims, 19 Drawing Sheets

(56) References Cited

U.S. PATENT DOCUMENTS

| | | | | |
|---|---|---|---|---|
| 7,472,374 | B1* | 12/2008 | Dillman | G06F 8/10 717/102 |
| 7,631,299 | B2* | 12/2009 | Kannenberg | G06F 8/70 705/4 |
| 7,716,077 | B1* | 5/2010 | Mikurak | G06Q 10/0631 705/7.12 |
| 7,971,180 | B2* | 6/2011 | Kreamer | G06Q 10/06 717/102 |
| 8,175,936 | B2* | 5/2012 | Ronen | G06Q 30/0641 705/27.2 |
| 8,225,282 | B1* | 7/2012 | Massoudi | G06F 8/34 717/121 |
| 8,887,130 | B2* | 11/2014 | Seetharaman | G06F 8/10 717/121 |
| 8,930,889 | B2* | 1/2015 | Kirby, Jr. | G06F 8/20 717/104 |
| 9,952,832 | B2* | 4/2018 | Sridhar | G06F 8/20 |
| 9,996,451 | B2* | 6/2018 | Andrejko | G06F 11/3684 |
| 10,001,975 | B2* | 6/2018 | Bharthulwar | G06F 11/3688 |
| 11,074,107 | B1* | 7/2021 | Nandakumar | G06F 8/10 |

OTHER PUBLICATIONS

Faping et al, "Research on Knowledge Push Method for Business Process Based on Multidimensional Hierarchical Context Model", IEEE, pp. 656-660 (Year: 2016).*
Catley et al., "Multi-Dimensional Temporal Abstraction and Data Mining of Medical Time Series Data: Trends and Challenges", IEEE, 4322-4325 (Year: 2008).*
Zenkert et al, "Towards Extractive Text Summarization using Multidimensional Knowledge Representation", IEEE, pp. 0826-0831 (Year: 2018).*
Bimonte et al, "Towards a Spatial Multidimensional Model", ACM, pp. 39-46 (Year: 2005).*
Arshd et al., "Applying Multidimensional Framework in Agile Software Development (MDFA)", ACM, pp. 1-8 (Year: 2021).*
Lin et al, "Using Goal Netto Model User Stories in Agile Software Development", IEEE, pp. 1-6 (Year: 2014).*
Buffardi, "Assessing Individual Contributions to Software Engineering Projects with Git Logs and User Stories", ACM, 650-656 (Year : 2020).*

* cited by examiner

SYSTEM AND METHOD TO GENERATE SOFTWARE DEVELOPMENT AND TESTING STORIES UTILIZING MULTI-DIMENSIONAL KNOWLEDGEBASE (MDK)

BACKGROUND

Technical Field

The inventive subject matter presented herein is generally directed towards the system and method to generate software development and testing stories. More particularly embodiments are related to, but not limited to, an artificial intelligence-based system and method to utilize multi-dimensional knowledgebase (MDK) to automatically generate software development and testing stories.

Description of the Related Art

Typically, the development process of a software system includes various steps such as software designing, coding, product management, project management, testing, etc. An analysis of the software system with respect to designing of the software system is extremely useful to understand the design requirements. Further, when developing a software system, it is difficult to predict how the software system will function under a real-world condition. It is also difficult to predict the security and risk vulnerabilities of the software system before and during the development process. In case, a software developer modifies the software system to adhere to real-world conditions and threats of attacks upon completion, then this additional effort consumes many hours of programming time and delays software system deployment which is very expensive.

For example, the development of software stories related to a medical device is very complicated as the factors impacting the software are multi-dimensional. Manual analysis alone is not sufficient as well as error-prone which can cause the medical devices to function incorrectly or incompletely. Also, the quality of human effort depends on individual capabilities and capacities hence not consistent in performance.

Thus, the existing methods of the software system development process are not able to reduce the risk and design time of the software system, from the beginning to the end of the software development process. The current software development process is manual, extremely costly, and time-consuming. This specification recognizes that there is a need for an artificial intelligence-based system and method to address the aforementioned issues of the software development process and reduce defects and risks associated with the performance of the software system and market release due to inconsistent and insufficient human capabilities and capacities. Further, there is a need for a system and method to generate software development and testing stories for medical device-related software to minimize the safety risks of the patient caused by software defects and maximizes the patient's and clinician's satisfaction.

Thus, in view of the above, there is a long-felt need in the software industry to address the described issues.

Further limitations and disadvantages of conventional and traditional approaches will become apparent to one of ordinary skill in the art through comparison of described systems with some aspects of the present disclosure, as set forth in the remainder of the present application and with reference to the drawings.

SUMMARY

System and method to generate software development and testing stories are provided and shown in and/or described in connection with the figures.

One aspect of the inventive subject matter relates to a system to generate software development and testing stories that includes a design specification system, an identification module, a creation module, a selection module, an analysis module, a development module, a feeding module, and a user computing device. The design specification system contains software design data. The collection module collects software design data from the design specification system. The identification module identifies a plurality of Base Software Business Logic Paths (BSBLP) that includes a plurality of base factors and a plurality of non-base factors. The identification module also identifies the base factors, the non-base factors, and a plurality of values of the base factors, and the non-base factors for each BSBLP. The creation module places the base factors, the non-base factors, and the values of the base factors, and the non-base factors for each BSBLP inside an Initial Factor List (IFL) to build one or more Multi-Dimensional Knowledgebases (MDK). The selection module selects a plurality of relevant BSBLP from the MDK for a subject software feature to be analyzed. The analysis module utilizes the relevant BSBLP selected by the selection module to perform a factor impact analysis on the subject software feature by processing the IFL for the relevant BSBLPs to develop a Final Factor List (FFL). The FFLs containing a list of a plurality of appliable non-base factors for the subject software feature. The development module generates the software development and testing stories by utilizing the FFL. The feeding module feeds the software development and testing stories back to the user computing device.

In an embodiment, the base factors include but are not limited to a time base factor, a location base factor, and a plurality of phase base factors.

In an embodiment, the non-base factors but are not limited to a hardware non-base factor, a user non-base factor, a plurality of existing software features, an external non-base factor, an environmental non-base factor.

In another embodiment, each of the MDK consists of the BSBLP.

In another embodiment, each of the BSBLP is a multi-dimensional space defined by the base factors and the non-base factors.

In another embodiment, the system is designed for use with software related to a medical device.

One aspect of the inventive subject matter relates to a computer-implemented method for generating a plurality of software development and testing stories. The computer-implemented method includes a step of collecting software design data from a design specification system through a collection module. The design specification system containing the software design data. The computer-implemented method includes a step of identifying a plurality of Base Software Business Logic Paths (BSBLP) through an identification module. The Base Software Business Logic Paths includes a plurality of base factors and a plurality of non-base factors. The identification module identifies the base factors, the non-base factors, and a plurality of values of the base factors, and the non-base factors for each BSBLP. The computer-implemented method includes a step of placing, by a creation module, the base factors, the non-base factors, and the values of the base factors, and the non-base factors for each BSBLP inside an Initial Factor List (IFL) to build one or more Multi-Dimensional Knowledgebases (MDK). The computer-implemented method includes a step of selecting, by a selection module, a plurality of relevant BSBLP from the MDK for a subject software feature to be analyzed. The computer-implemented method includes a step of performing, by an analysis module, a factor impact analysis on the subject software feature by processing the IFL for the relevant BSBLPs to develop a Final Factor List (FFL). The FFLs containing a list of a plurality of appliable non-base factors for the subject software feature. The computer-implemented method includes a step of generating, by a development module, software development, and testing stories by utilizing the FFL. The computer-implemented method includes a step of feeding, by a feeding module, software development, and testing stories back to a user computing device.

In an embodiment, the base factors include but are not limited to a time base factor, a location base factor, and a plurality of phase base factors.

In an embodiment, the non-base factors but are not limited to a hardware non-base factor, a user non-base factor, a plurality of existing software features, an external non-base factor, an environmental non-base factor.

In another embodiment, each of the MDK consists of the BSBLP.

In another embodiment, each of the BSBLP is a multi-dimensional space defined by the base factors and the non-base factors.

Accordingly, one advantage of the present inventive subject matter is that it provides a computerized AI analytical model that utilizes the multi-dimensional knowledgebase (MDK) to automate the generation of comprehensive software development and testing stories.

Accordingly, one advantage of the present inventive subject matter is that it creates traceability for a plurality of design requirements and a plurality of regulation compliances.

Accordingly, one advantage of the present inventive subject matter is that it uses artificial intelligence to reduce software design time, cost, and risk.

Accordingly, one advantage of the present inventive subject matter is that it improves the performance of a software system and related hardware which leads to higher user satisfaction and lower safety risks.

Accordingly, one advantage of the present inventive subject matter is that it replaces or enhances manual software designing to reduce defects and risk of product performance and market release.

Accordingly, one advantage of the present inventive subject matter is that it minimizes patients' safety risks caused by software defects.

Accordingly, one advantage of the present inventive subject matter is that it generates design specification data based on the medical data received from the patient and the clinician.

Accordingly, one advantage of the present inventive subject matter is that it develops and tests the medical device-related software to minimize the safety risks of the patient caused by software defects and its related hardware, meets the regulation and compliance requirements, and maximizes the patient's and clinician's satisfaction.

These features and advantages of the present disclosure may be appreciated by reviewing the following description of the present disclosure, along with the accompanying figures wherein like reference numerals refer to like parts.

BRIEF DESCRIPTION OF THE DRAWINGS

The accompanying drawings illustrate the embodiments of systems, methods, and other aspects of the disclosure. A person with ordinary skills in the art will appreciate that the illustrated element boundaries (e.g., boxes, groups of boxes, or other shapes) in the figures represent an example of the boundaries of such elements. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope, wherein similar designations denote similar elements, and in which.

DETAILED DESCRIPTION

The present disclosure is best understood with reference to the detailed figures and description set forth herein. Various embodiments of the present systems and methods have been discussed with reference to the figures. However, those skilled in the art will readily appreciate that the detailed description provided herein including the figures are presented for explanatory purposes and the embodiments extend beyond the currently described embodiments. For instance, the teachings and results presented in any particular described application may yield multiple alternative approaches and may be implemented in any suitable manner.

The described embodiments may be implemented manually, automatically, and/or a combination of thereof. The term "method" refers to manners, means, techniques, and procedures for accomplishing any task including, but not limited to, those manners, means, techniques, and procedures either known to the person skilled in the art or readily developed from existing manners, means, techniques and procedures by practitioners of the art to which the embodiments pertains. Persons skilled in the art will envision many other possible variations that are within the scope of the claimed subject matter.

Figure 1:
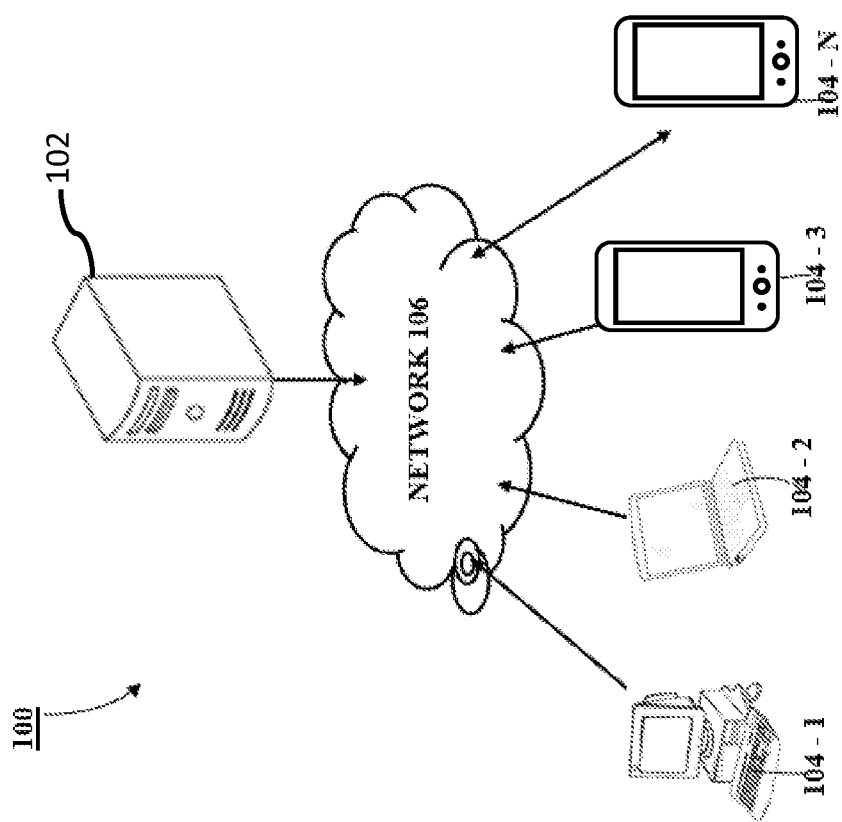
FIG. 1 illustrates a network implementation of the present system and method to generate a plurality of software development and testing stories in accordance with at least one embodiment of the claimed subject matter.

FIG. 1 illustrates a network implementation 100 of the present system and method to generate a plurality of software development and testing stories in accordance with at least one embodiment of the claimed subject matter. Although the present subject matter is explained considering that the present system 102 is implemented on a server, it may be understood that the present system 102 may also be implemented in a variety of user computing systems, such as a laptop computer, a desktop computer, a notebook, a workstation, a mainframe computer, a server, a network server, and the like. It will be understood that the present system 102 may be accessed by multiple users through one or more user computing devices 104-1, 104-2 . . . 104-N, collectively referred to as a user computing device 104 hereinafter, or applications residing on the user computing device 104. Examples of the user computing device 104 may include but are not limited to, a portable computer, a personal digital assistant, a handheld or mobile device, smart devices, and a workstation. The computing devices 104 are communicatively accessible to the present system 102 through a network 106.

In one implementation, the network 106 may be a wireless network, a wired network, or a combination thereof. The network 106 can be implemented as one of the different types of networks, such as an intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

Figure 2:
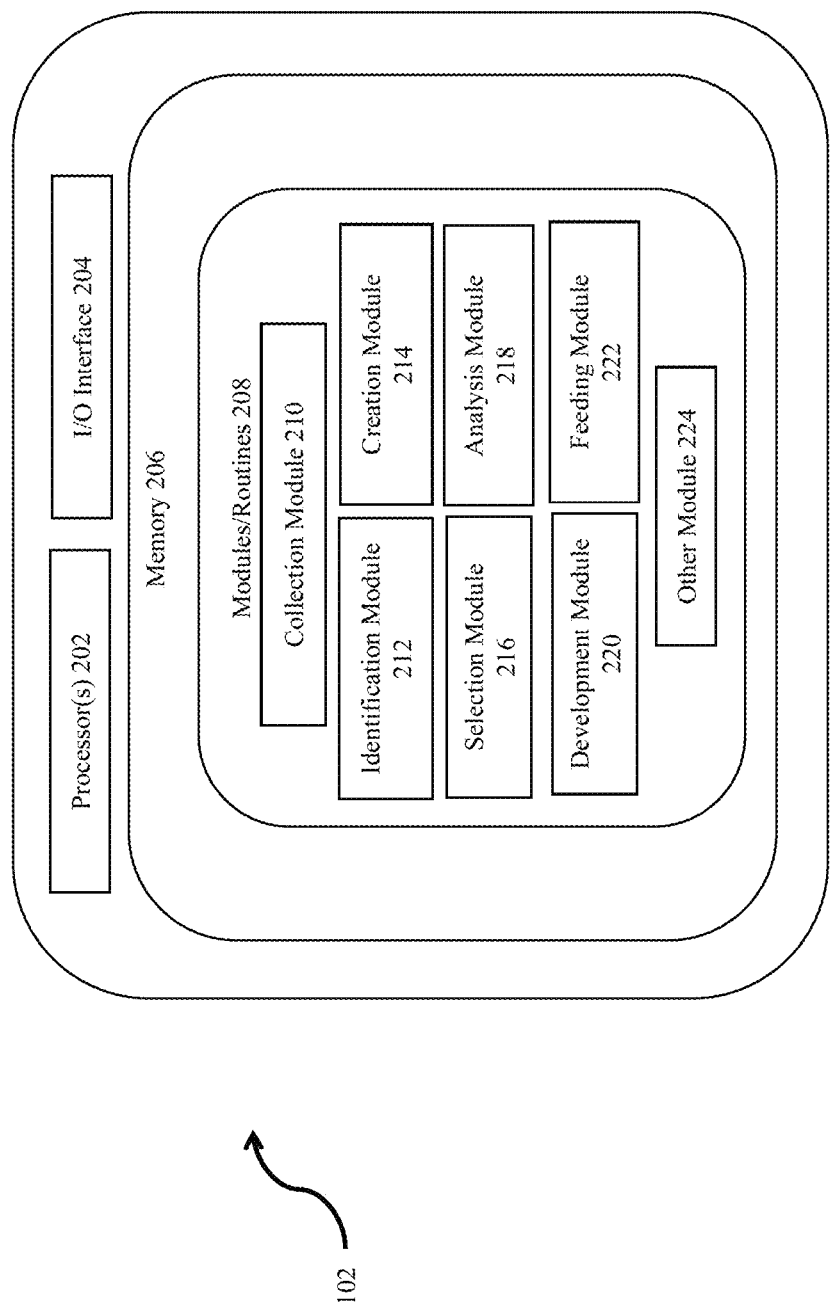
FIG. 2 illustrates the present system to generate a plurality of software development and testing stories in accordance with at least one embodiment of the claimed subject matter.

FIG. 2 illustrates the present system 102 to generate a plurality of software development and testing stories in accordance with at least one embodiment of the claimed subject matter and can be viewed in conjunction with FIG. 1. The system 102 includes a design specification system 402 (shown in FIG. 3B), at least one processor 202, an input/output (I/O) interface 204, a memory 206, and a user computing device 104. The design specification system 402 contains software design data. The processor 202 is implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with a user directly or through the user computing device 104. Further, the I/O interface 204 may enable the system 102 to communicate with other user computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read-only memory (ROM), erasable programmable ROM, flash memories, hard disks, optical disks, and magnetic tapes. The memory 206 includes various modules 208.

The modules 208 include routines, programs, objects, components, data structures, etc., which perform particular tasks or implement particular abstract data types. In one implementation, the modules 208 include a collection module 210, an identification module 212, a creation module 214, a selection module 216, an analysis module 218, a development module 220, a feeding module 222, and other module 224. The other modules 222 may include programs or coded instructions that supplement applications and functions of the system 102.

In one implementation, the collection module 210 collects software design data from the design specification system 402. The identification module 212 identifies a plurality of Base Software Business Logic Paths (BSBLP) that includes a plurality of base factors and a plurality of non-base factors. In an embodiment, the base factors include but are not limited to a time base factor, a location base factor, and a plurality of phase base factors. In an embodiment, the non-base factors but are not limited to a hardware non-base factor, a user non-base factor, a plurality of existing software features, an external non-base factor, an environmental non-base factor. Within a BSBLP, all base factors should be applicable for each non-base factor. The identification module 212 also identifies the base factors, the non-base factors, and a plurality of values of the base factors, and the non-base factors for each BSBLP. The creation module 214 places the base factors, the non-base factors, and the values of the base factors, and the non-base factors for each BSBLP inside an Initial Factor List (IFL) to build one or more Multi-Dimensional Knowledgebases (MDK) 412 (shown in FIG. 3B). In another embodiment, each of the MDK 412 consists of the BSBLP. In an embodiment, each of the BSBLP is a multi-dimensional space defined by the base factors and the non-base factors. The selection module 216 selects a plurality of relevant BSBLP from the MDK 412 for a subject software feature to be analyzed. The analysis module 218 utilizes the relevant BSBLP selected by the selection module to perform a factor impact analysis on the subject software feature by processing the IFL for the relevant BSBLPs to develop a Final Factor List (FFL). The FFLs containing a list of a plurality of appliable non-base factors for the subject software feature. The development module 220 generates the software development and testing stories by utilizing the FFL. The feeding module 222 feeds the software development and testing stories back to the user computing device 104. Thus, the FFL is used to generate software development and testing stories. For each element in the FFL, the possible element values are analyzed. For each BSBLP phase and phase transition, the software development stories are created for the subject software feature by using the FFL.

Figure 3A:
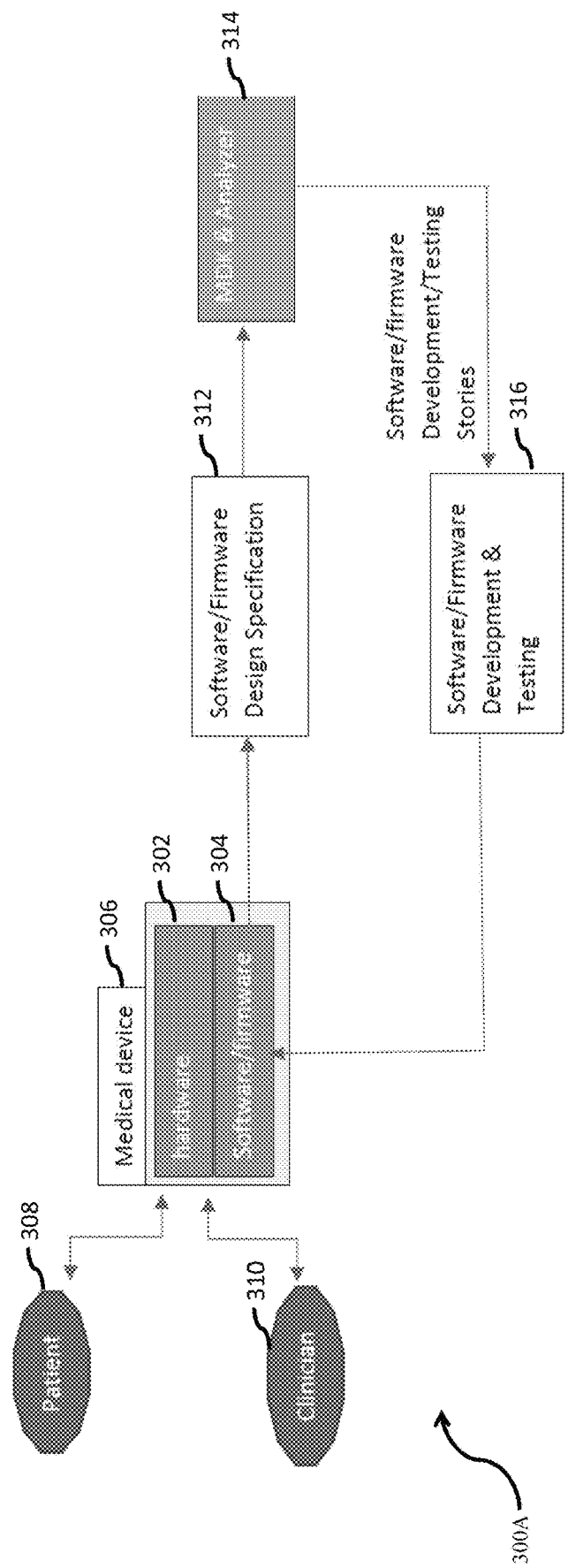
FIG. 3A illustrates an exemplary view of the present system executing various instructions related to hardware, software, and user interface of a medical device in accordance with at least one embodiment of the claimed subject matter.

In another embodiment, the system 102 is designed for use with software related to a medical device (MD). However, it is understood that software related to other devices or purposes can utilize the present system 102 within the illustrated embodiments. The present system 102 can be modified to use for other software design, development, and testing. FIG. 3A illustrates an exemplary view 300A of the present system executing various instructions related to hardware 302, software 304, and user interface of a medical device 306 in accordance with at least one embodiment of the claimed subject matter. In an embodiment, the medical device (MD) 306 is referred to as any device that's intended to be used for medical purposes. In use, the medical device (MD) 306 receives medical data from a patient 308 and a clinician 310. According to an embodiment herein, the software 304 or firmware related to medical device 306 can be a software that is either embedded to run the medical device hardware, for example, the software 304 used to drive or control the motors and the pumping of medication in an infusion pump or a standalone software such as Software As a Medical Device (SaMD) which may be a software that allows a smartphone to view images obtained from a magnetic resonance imaging (MRI) medical device for diagnostic purposes. Again, the teachings here can be modified for other presently known or future software and hardware interfaces. The software 304 generates design specification data 312 based on the medical data received from the patient 308 and the clinician 310. The design specification data 312 further analyzed and processed by an MDK and analyzer 314. The software/firmware development and testing stories are further processed for software development and testing 316 and transmitted to the software/firmware 304.

In other embodiment, the present system 102 is an artificial intelligence-based analytical model which is used to develop and test the MD related software that can minimize the safety risks of the patient 408 caused by software defects and its related hardware, meet the regulation/compliance requirements and maximize user's satisfaction. The development of medical device software stories is very complicated as the factors impacting the software are multi-dimensional.

According to an embodiment herein, the present system 102 utilizes the multi-dimensional knowledgebase to identify all the applicable factors that could potentially impact the subject software features and then generates comprehensive software development stories based on the factor analysis and can produce reliable outputs consistently. This way the present system 102 reduces the number of missing factors and improves the correctness and completeness of medical device functions, which assure the product can complete the mission-critical tasks in its ever-changing operating environment.

Figure 3B:
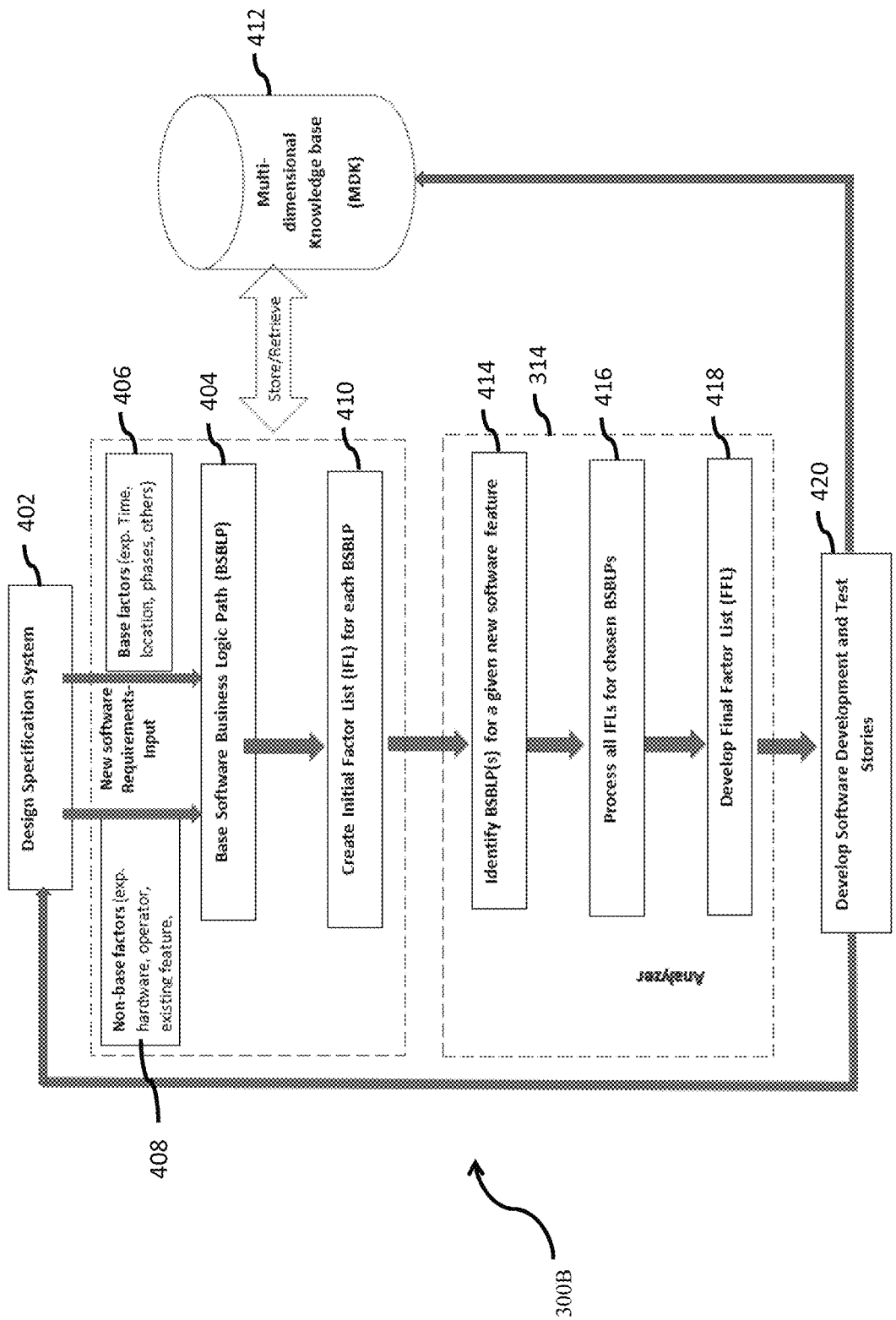
FIG. 3B illustrates a flow chart of an overview operation performed in accordance with at least one embodiment of the claimed subject matter.

FIG. 3B illustrates a flow chart 300B of an overview operation performed in accordance with at least one embodiment of the claimed subject matter and can be viewed in conjunction with FIG. 2. The computer-implemented method generates a plurality of software development and testing stories. The computer-implemented method includes a step of collecting software design data including requirements and other design specifications from a design specification system 402 through a collection module. The design specification system contains 402 software design data. The computer-implemented method includes a step of identifying a plurality of Base Software Business Logic Paths (BSBLP) 404 for the software through an identification module. For example, a pacemaker can perform both dual-chamber pacing and single-chamber pacing therapies, each therapy is a BSBLP. A dialysate machine can perform various renal replacement therapies, and each therapy is a BSBLP. Each BSBLP is independent of the rest and cannot concurrently run with any other BSBLP. The Base Software Business Logic Paths 404 includes a plurality of base factors 406 and a plurality of non-base factors 408. In an embodiment, the base factors 406 include but are not limited to a time base factor, a location base factor, and a plurality of phase base factors. In an embodiment, the non-base factors 408 but are not limited to a hardware non-base factor, a user non-base factor, a plurality of existing software features, an external non-base factor, an environmental non-base factor.

The identification module identifies the base factors 406, the non-base factors 408, and a plurality of values of the base factors 406, and the non-base factors 408 for each BSBLP 404. Within a BSBLP, all base factors should be applicable for each non-base factor. The computer-implemented method includes a step of placing, by a creation module, the base factors 406, the non-base factors 408, and the values of the base factors 406, and the non-base factors 408 for each BSBLP 404 inside an Initial Factor List (IFL) 410 to build one or more Multi-Dimensional Knowledgebases (MDK) 412. The Multi-Dimensional Knowledgebase (MDK) which consists of all the BSBLPs for the subject software. The computer-implemented method includes a step of selecting, by a selection module, a plurality of relevant BSBLP from the MDK 412 for a subject software feature 414 to be analyzed in the analyzer 314. Examples of the subject software feature include but are not limited to adding a new scale to a dialysis machine, changing the therapy target area of the patient's body for pain management therapy. At block 416, the computer-implemented method includes a step of performing a factor impact analysis on the subject software feature by processing the IFL for the relevant BSBLPs to develop a Final Factor List (FFL) 418. The FFLs containing a list of a plurality of appliable non-base factors for the subject software feature. The computer-implemented method includes a step of generating, by a development module, software development, and testing stories 420 by utilizing the FFL. For each element in the FFL, analyze the possible element values. For each BSBLP phase and phase transition, create software development stories for the target software feature by using the FFL The computer-implemented method includes a step of feeding software development and testing stories back to the user computing device 104.

Figure 3C:
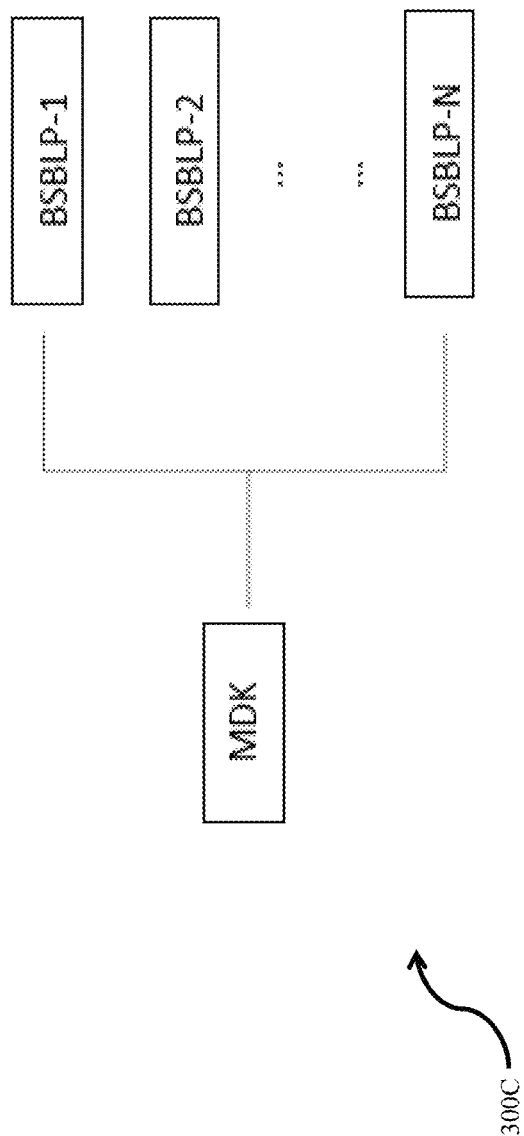
FIG. 3C illustrates a flow chart of a relationship between Multi-Dimensional Knowledgebase (MDK) and Base Software Business Logic Paths (BSBLP) in accordance with at least one embodiment of the claimed subject matter.

FIG. 3C illustrates a flow chart 300C of a relationship between Multi-Dimensional Knowledgebase (MDK) and Base Software Business Logic Paths (BSBLP) in accordance with at least one embodiment of the claimed subject matter. In other embodiments, each MDK consists of a set of subcomponents called Base Software Business Logic Paths (BSBLP). For example, if a pacemaker can perform both dual-chamber pacing and single-chamber pacing, each pacing is a BSBLP. A dialysate machine can perform a set of renal replacement therapies, and each therapy is a BSBLP. Each BSBLP is independent of the rest and cannot concurrently run with any other BSBLP.

Figure 3D:
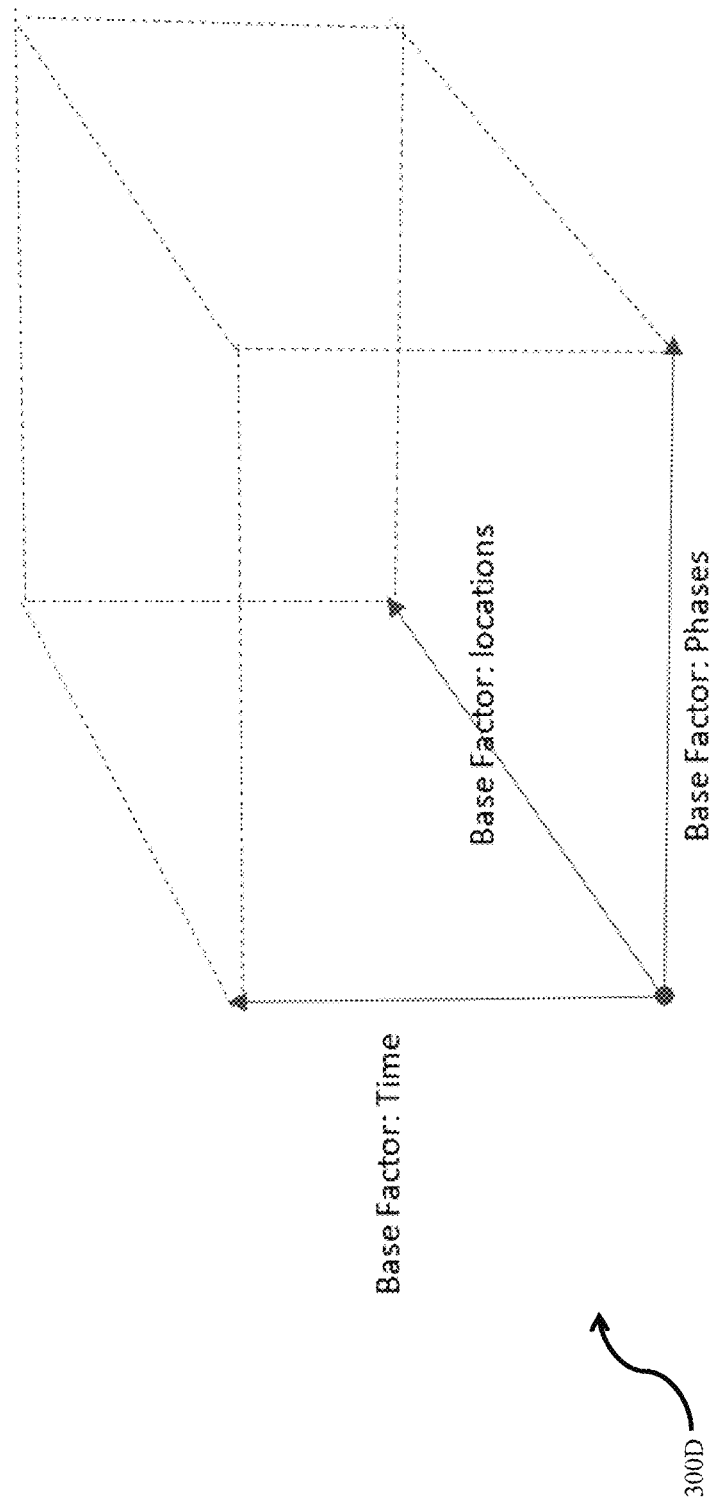
FIG. 3D illustrates a graphical representation of BSBLP and a 3-D Space of the BSBLP as an example (formed by the base factors) in accordance with at least one embodiment of the claimed subject matter.

FIG. 3D illustrates a graphical representation 300D of BSBLP and a 3-D Space of the BSBLP as an example (formed by the base factors) in accordance with at least one embodiment of the claimed subject matter. Each BSBLP is a multi-dimensional space defined by the base factors and non-base factors. X number of base factors define an X-dimensional space. In one of the embodiments, the present system uses three base factors as an example which defines a 3-D space. All software features of the BSBLP operates in this Space. In the example of a pacemaker, it has a pacing BSBLP, the location base factor could be a surgery room where the device gets implanted, a clinician office where the device gets a periodic check, patient's home/bedrooms, exercise fitness room, cars, outdoors, airports, hospital, etc. The time base factor could be described in a time series on a one-month scale. In an embodiment, the phase base factor includes various phases such as storage phase, set up phase, therapy delivery phase, therapy off phase, near the end of life phase, end of life phase.

Figure 3E:
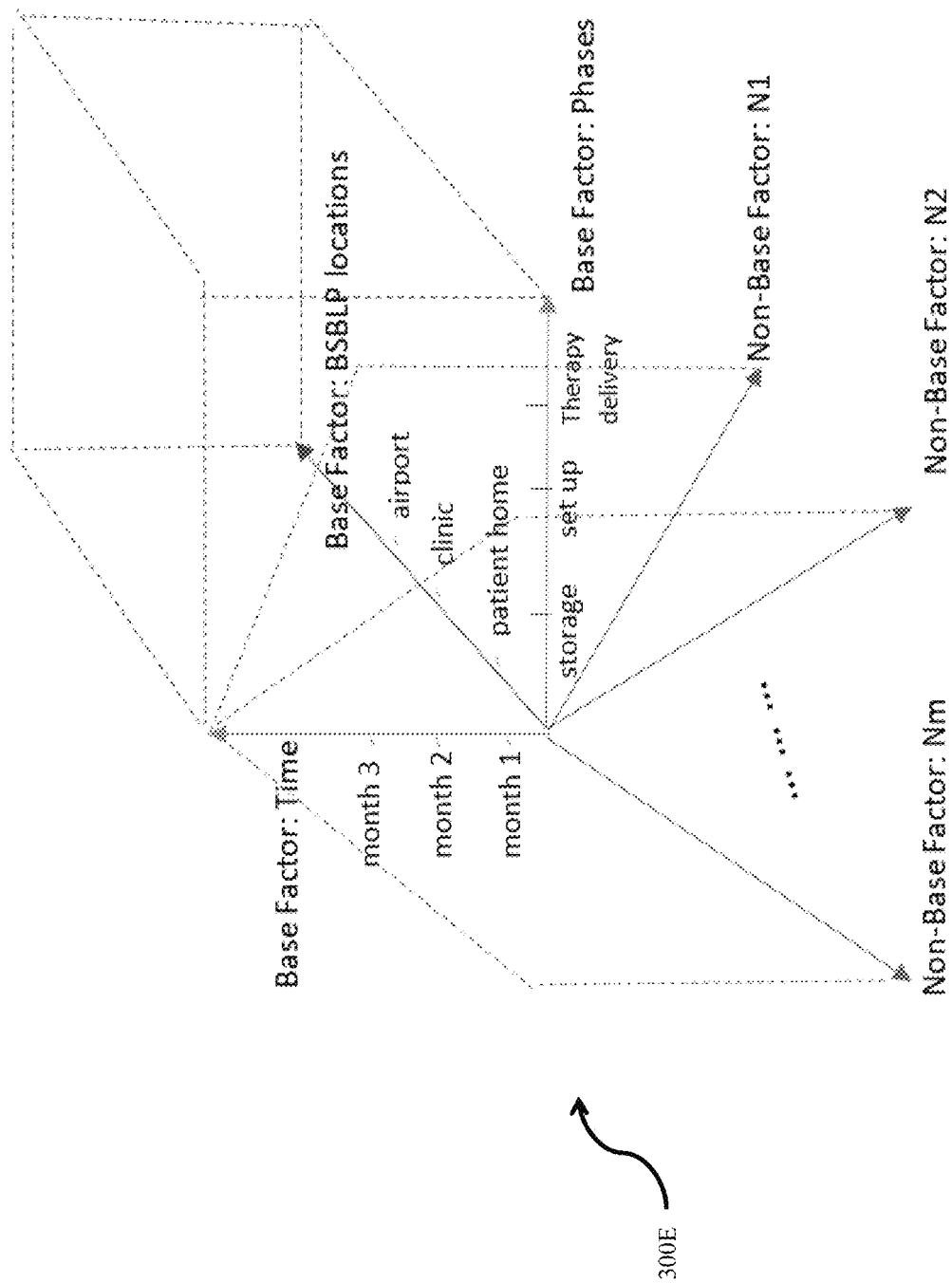
FIG. 3E illustrates a graphical representation of non-base factors and multi-dimension space for the BSBLP in accordance with at least one embodiment of the claimed subject matter.
Figure 3F:
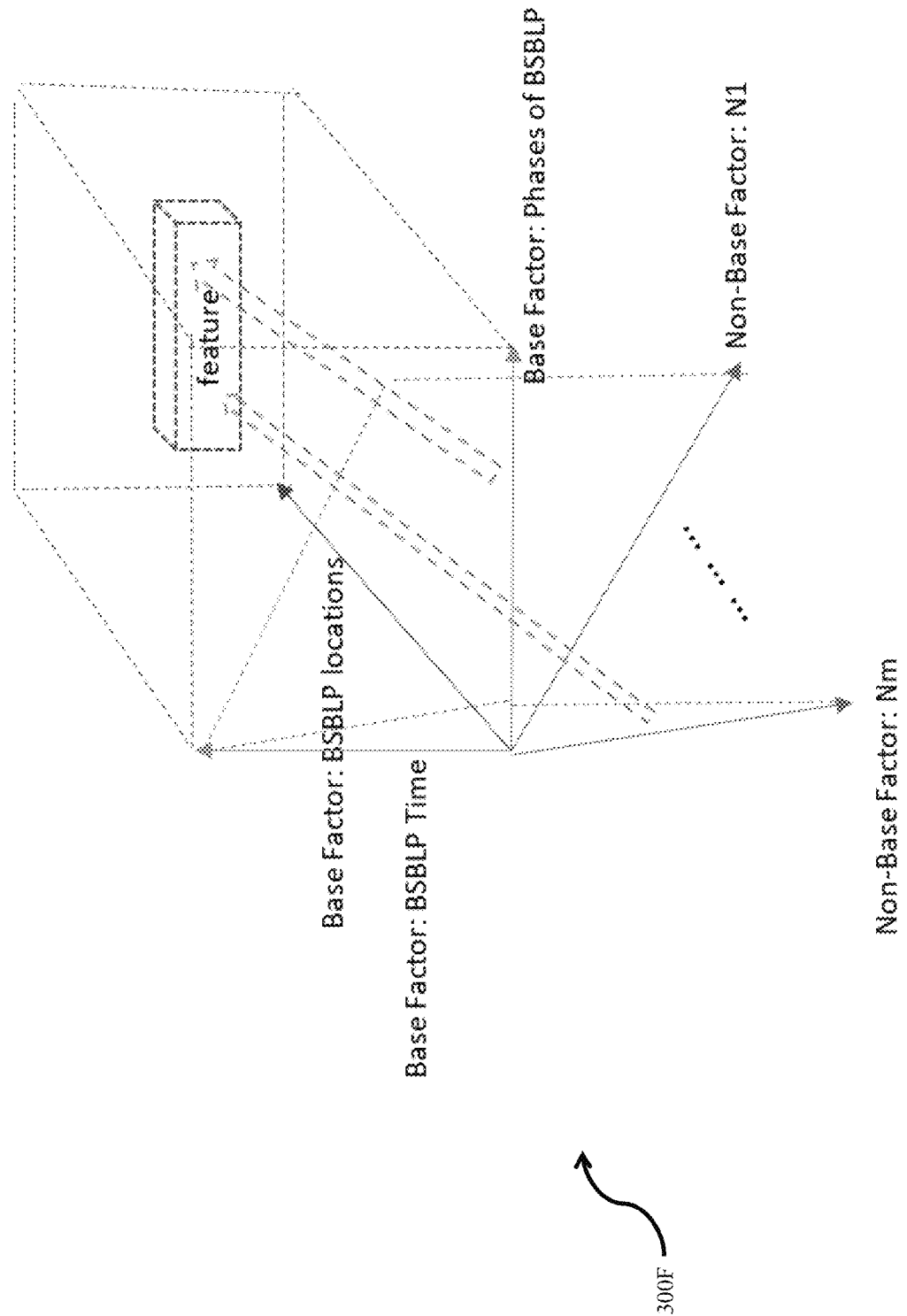
FIG. 3F illustrates a graphical representation of an impact of non-base factor dimension on the subject software feature in accordance with at least one embodiment of the claimed subject matter.
Figure 3G:
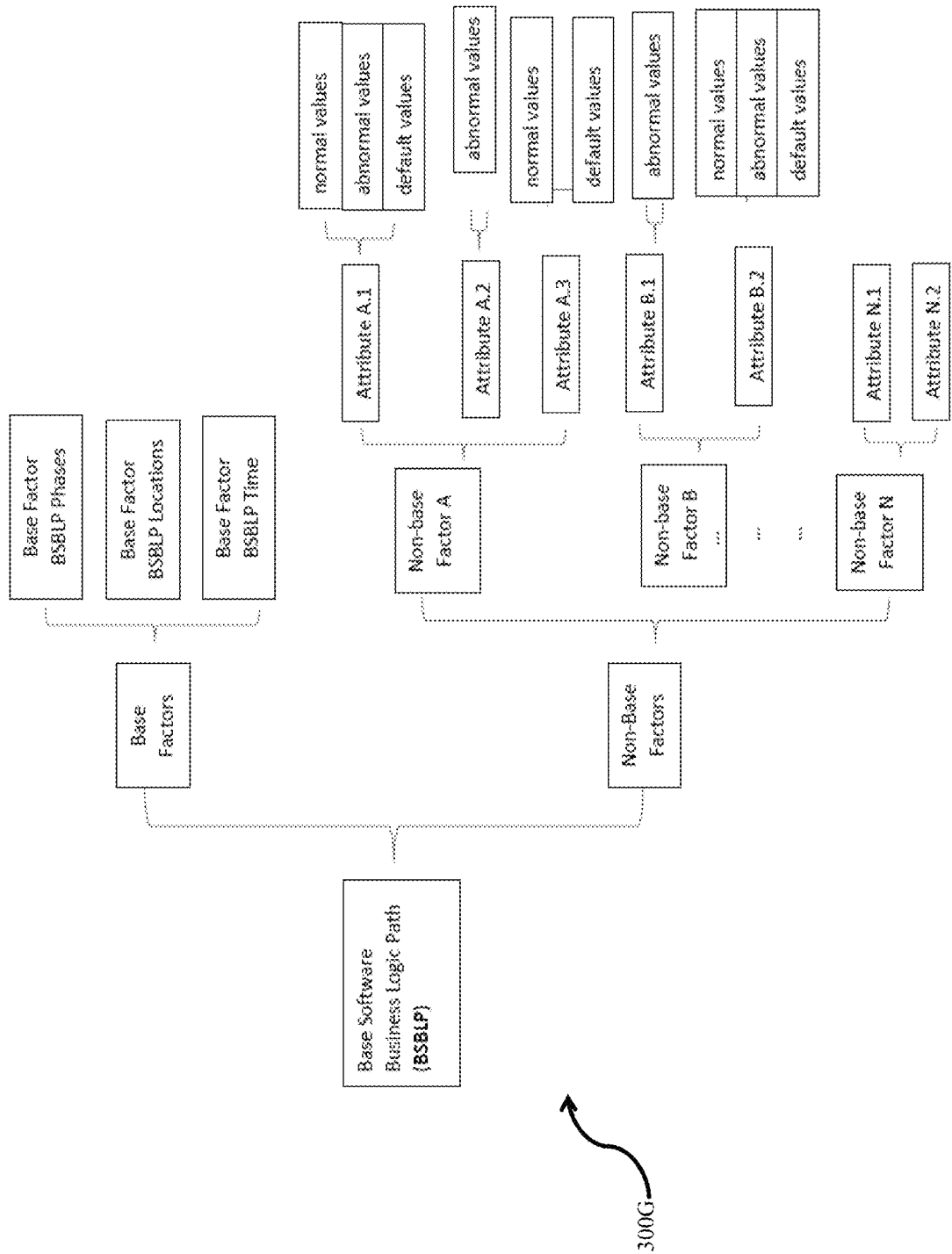
FIG. 3G illustrates a graphical representation of a structure of a BSBLP, and factors and factor attributes in accordance with at least one embodiment of the claimed subject matter.

FIG. 3E illustrates a graphical representation 300E of non-base factors and multi-dimension space for the BSBLP in accordance with at least one embodiment of the claimed subject matter. In an embodiment, each non-base factor adds an extra dimension to space. For example, in the case of pacemaker performing pacing (BSBLP), the hardware non-base factors can include a battery, capacitor, leads (connecting the device to patient's heart tissue); the software non-base factors can be heart rhythm monitoring, history data recording, secure communication with external commands, etc. The external non-base factor could be the programmer (which is an external portable device that can interact with the pacing device to set it up and retrieve the history pacing report from the pacing device). The environmental non-base factor could be ambient (room) temperature, humidity, and radio frequency interference (like airport security scanning, or patient goes into MRI scanning which produces strong interference to the device). Other non-base factors could include patient, clinician, etc. FIG. 3F illustrates a graphical representation 300F of an impact of non-base factor dimension on the subject software feature in accordance with at least one embodiment of the claimed subject matter. If a BSBLP's base factors can be applicable for Feature A, all the non-base factors in that BSBLP can potentially impact/ interact with this feature. For example, a pacemaker has two BSBLPs, single-chamber pacing, and dual-chamber pacing. If Feature A for the pacemaker is only compatible with all the base factors of dual-chamber pacing, all the non-base factors of the dual-chamber pacing BSBLP could be potentially applicable for Feature A while the non-base factors of the single-chamber pacing BSBLP won't. FIG. 3G illustrates a graphical representation 300G of a structure of a BSBLP, and factors and factor attribute in accordance with at least one embodiment of the claimed subject matter. In an embodiment, the various non-base factors include corresponding factor attributes. Each of the factor attributes includes at least one of normal values, abnormal values, default values, and/or a combination thereof.

In the case of a pacing BSBLP, examples of the non-base factors include but are not limited to the following attributes and values mentioned after a colon. For a battery, i) Battery State: valid or invalid; ii) Battery Percentage: 100% to 0% (90% plus is called full stage, 60 to 80% is a normal stage, 40 to 60% is a warning, 20 to 40% is an early indicator of low power state, 20% below is explant indicator state). For a lead, i) Lead state: normal, warning (some early signs of internal fracture but the device can still deliver the therapy), and fractured (lead is broken, and therapy is not delivered). For a patient, i) Patient heart rhythm: slow (less than 50 beats per minute, regular {greater than 50 but less than 120}, fast (greater than 120 but less than 140), and life-threatening fast (greater than 140); ii) Patient position: lying, sitting, standing; ii0) Patient movement: still, walk, run. For device monitoring, i) Monitoring state: disable or enable; ii) Monitoring data state: invalid reading or valid reading. For an operator, i) The presence of the Operator: yes or no.

Figure 4A:
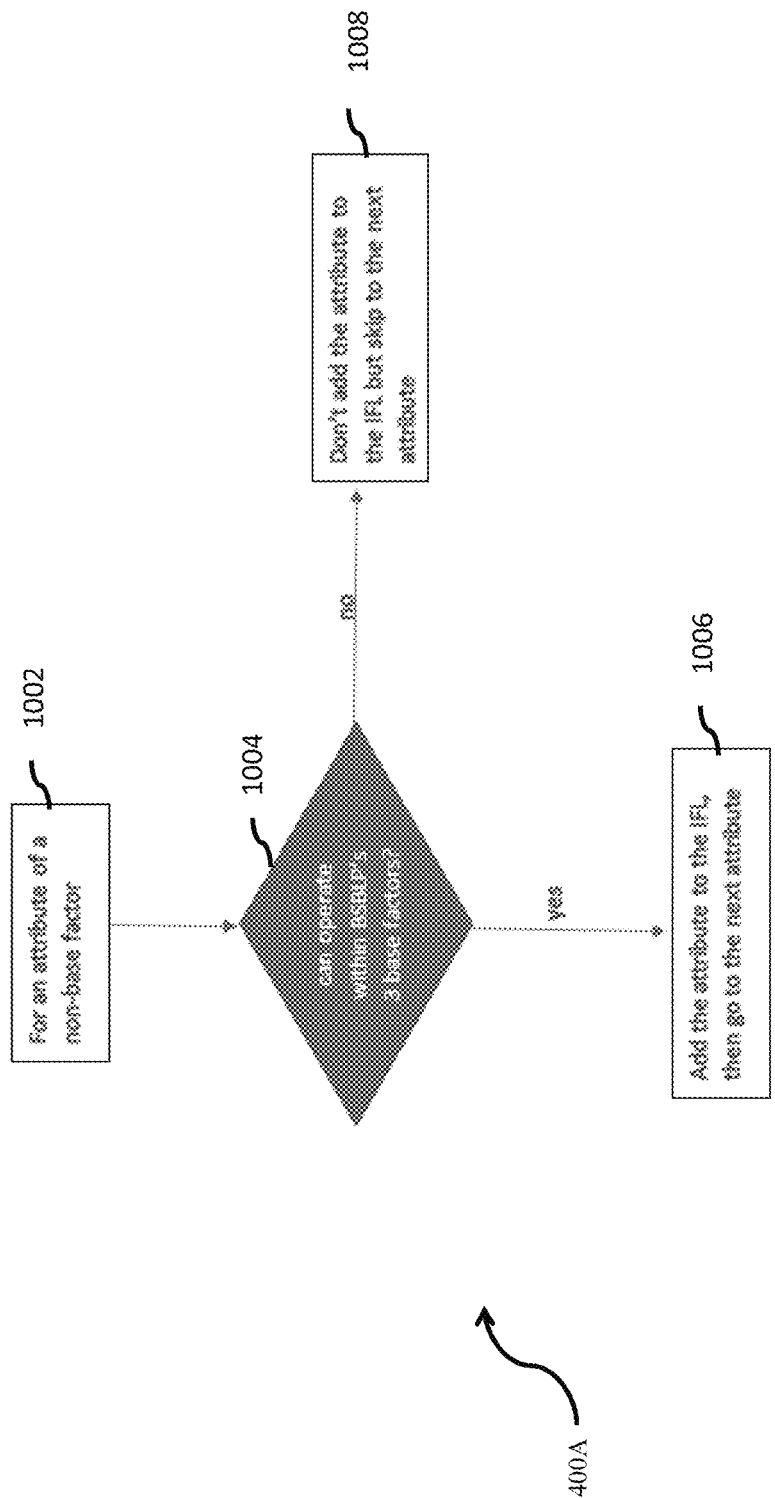
FIG. 4A illustrates a flow chart to create an IFL for a BSBLP in accordance with at least one embodiment of the claimed subject matter.
Figure 4B:
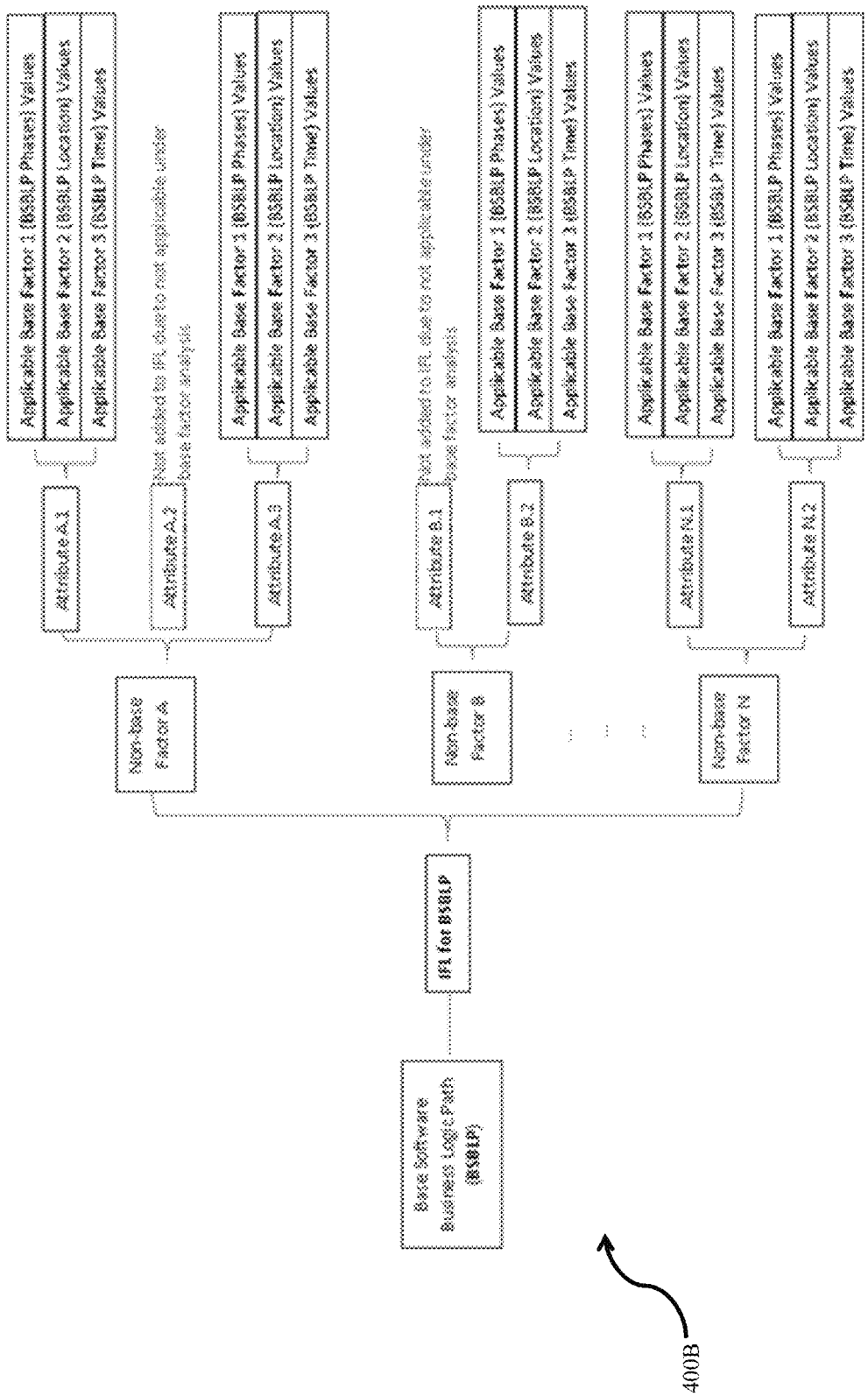
FIG. 4B illustrates a flow chart of a structure of Initial Factor List (IFL) for a given BSBLP based on FIG. 3F in accordance with at least one embodiment of the claimed subject matter.
Figure 5A:
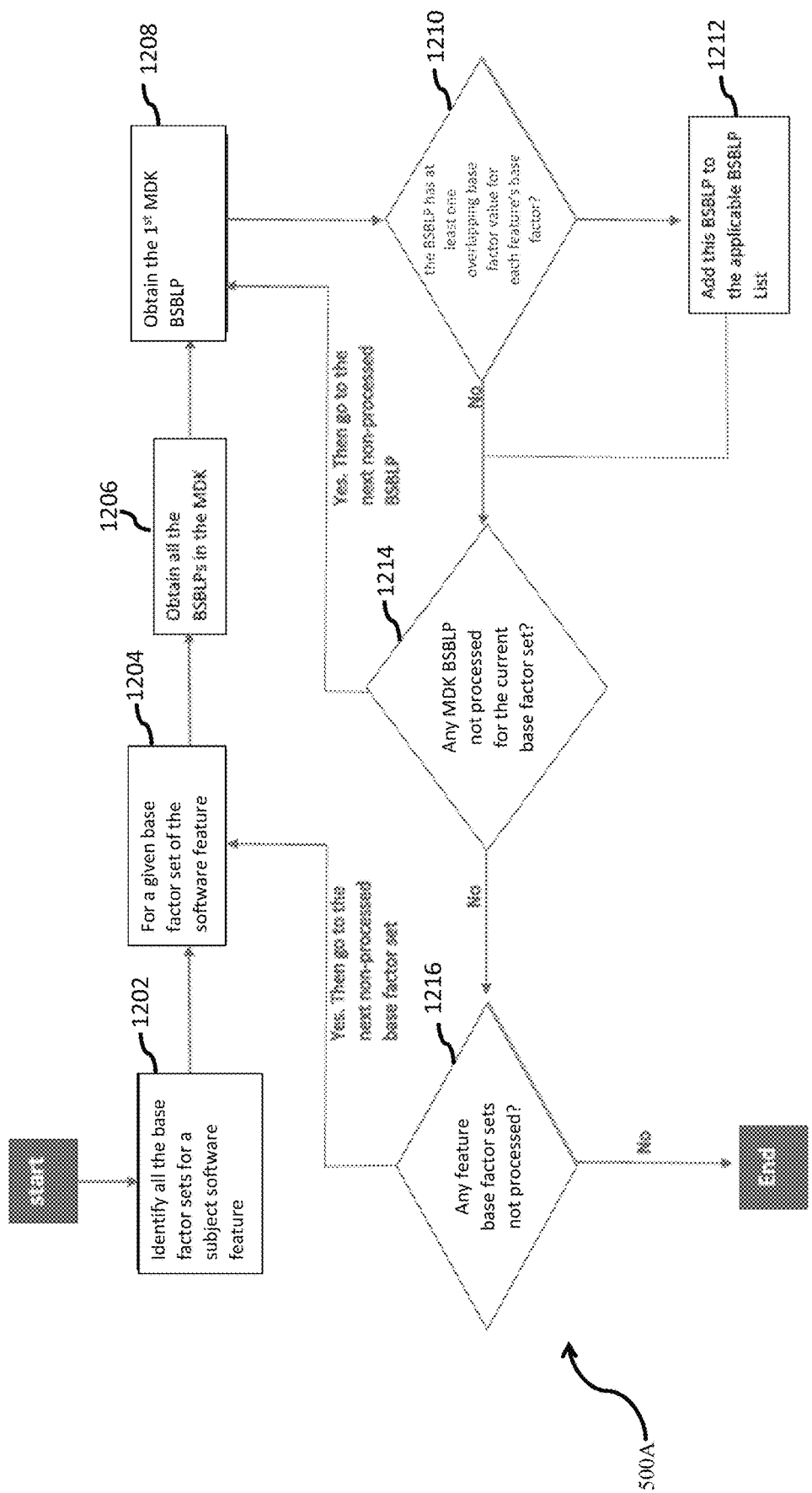
FIG. 5A illustrates a flow chart to identify the BSBLPs for a subject software feature in accordance with at least one embodiment of the claimed subject matter.

FIG. 4A illustrates a flow chart 400A of a method to create an IFL for a BSBLP in accordance with at least one embodiment of the claimed subject matter. At step 1002, the IFL creation step is initiated for an attribute of a non-base factor. At step 1004, the method determines whether the non-base factor can operate within BSBLP's 3 base factors. At step 1006, in case it is determined that the non-base factor can operate within BSBLP's 3 base factors, the attribute is added to the IFL, then proceeds for the next attribute. At step 1008, in case it is determined that the non-base factor cannot operate within BSBLP's 3 base factors, the attribute is not added to the IFL and the method skips to the next attribute. FIG. 4B illustrates a flow chart 400B of a structure of Initial Factor List (IFL) for a given BSBLP based on FIG. 3F in accordance with at least one embodiment of the claimed subject matter. In an embodiment, each BSBLP has only one IFL. FIG. 5A illustrates a flow chart 500A to identify the BSBLPs for a subject software feature in accordance with at least one embodiment of the claimed subject matter. At step 1202, sets related to all the base factor for a subject software feature are identified. At step 1204, sets related to a given base factor set of the software feature is also identified. At step 1206, all the BSBLPs in the MDK are obtained. At step 1208, the first MDK BSBLP is obtained. At step 1210, it is determined whether the BSBLP has at least one overlapping base factor value for each feature's base factor. At step 1212, in case, it is determined that the BSBLP has at least one overlapping base factor value for each feature's base factor, then this BSBLP is added to an applicable BSBLP list. At step 1214, in case, it is determined that the BSBLP has not at least one overlapping base factor value for each feature's base factor, then the method further determines whether any MDK BSBLP is processed for the current base factor set. In case, the method determines that any MDK BSBLP is processed for the current base factor set, then the step 1208 is repeated. At step 1216, in case, the method determines that any MDK BSBLP is not processed for the current base factor set, then the method determines if any feature base factor sets are processed or not. In case, the method determines that any feature base factor sets are processed, then the method proceeds to the next non-processed base factor set.

Figure 5B:
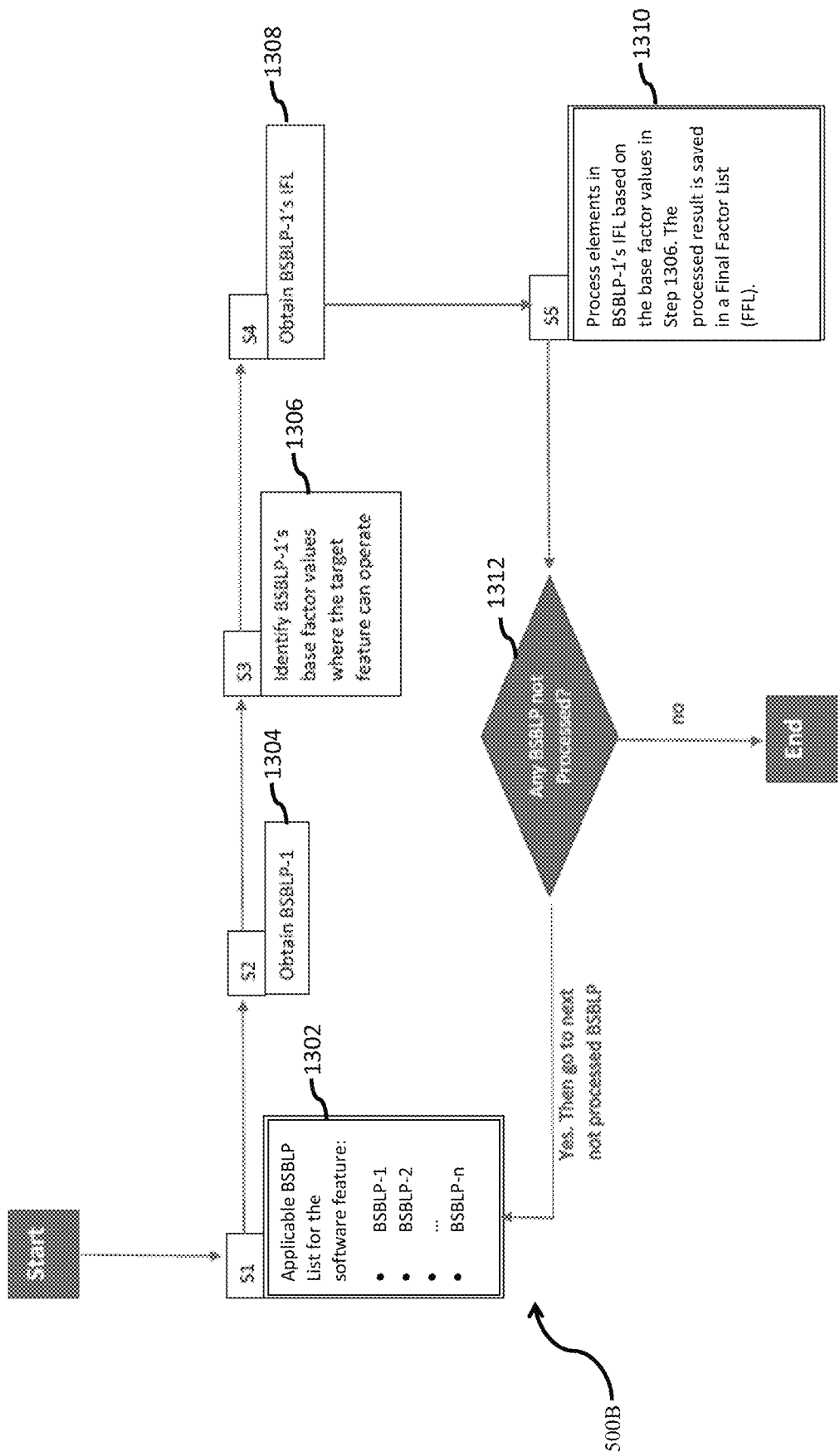
FIG. 5B illustrates a flow chart of IFL for a subject software feature to come up with FFL in accordance with at least one embodiment of the claimed subject matter.
Figure 5C:
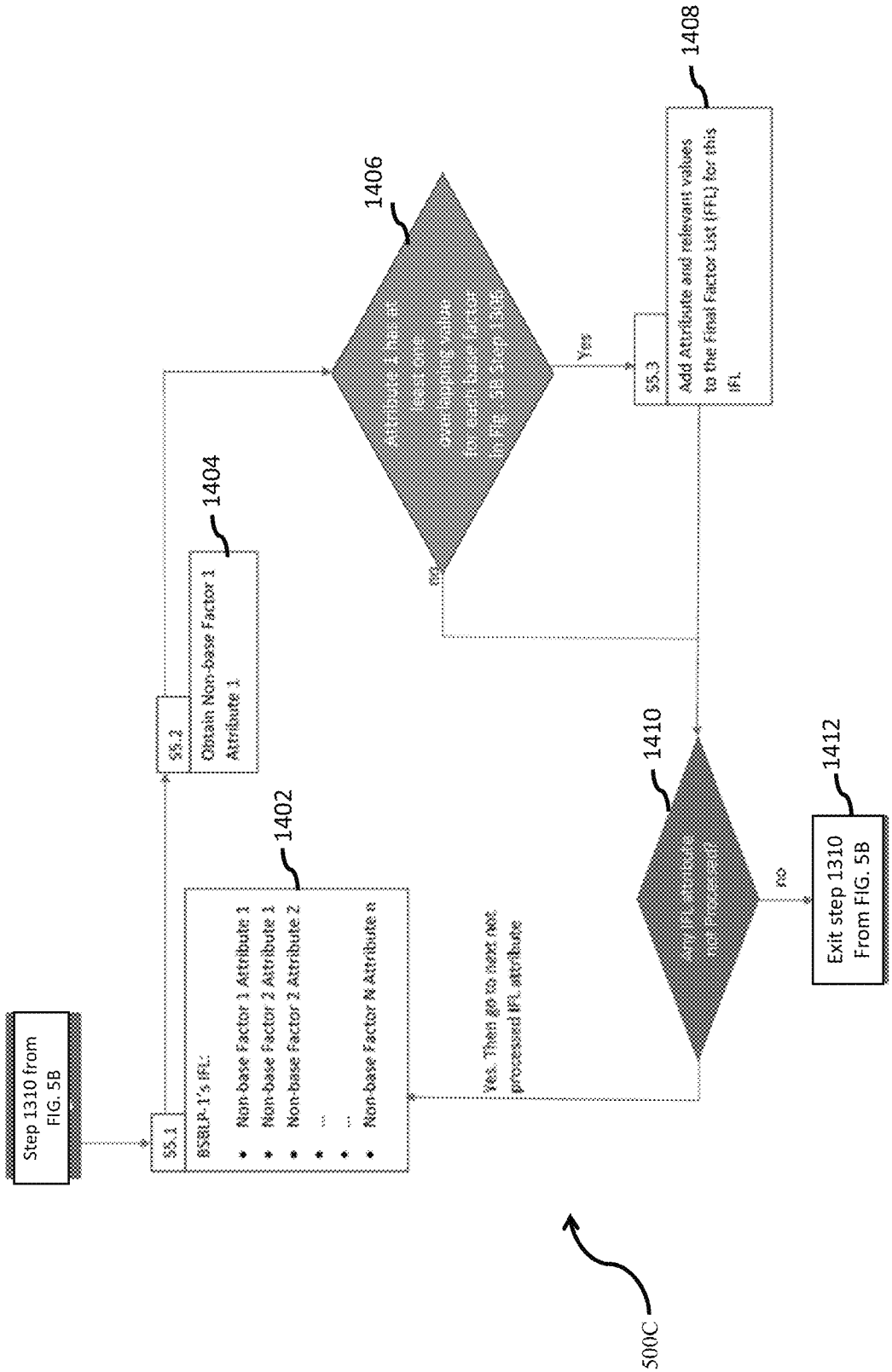
FIG. 5C illustrates a flow chart of IFL for FFL in accordance with at least one embodiment of the claimed subject matter.
Figure 5D:
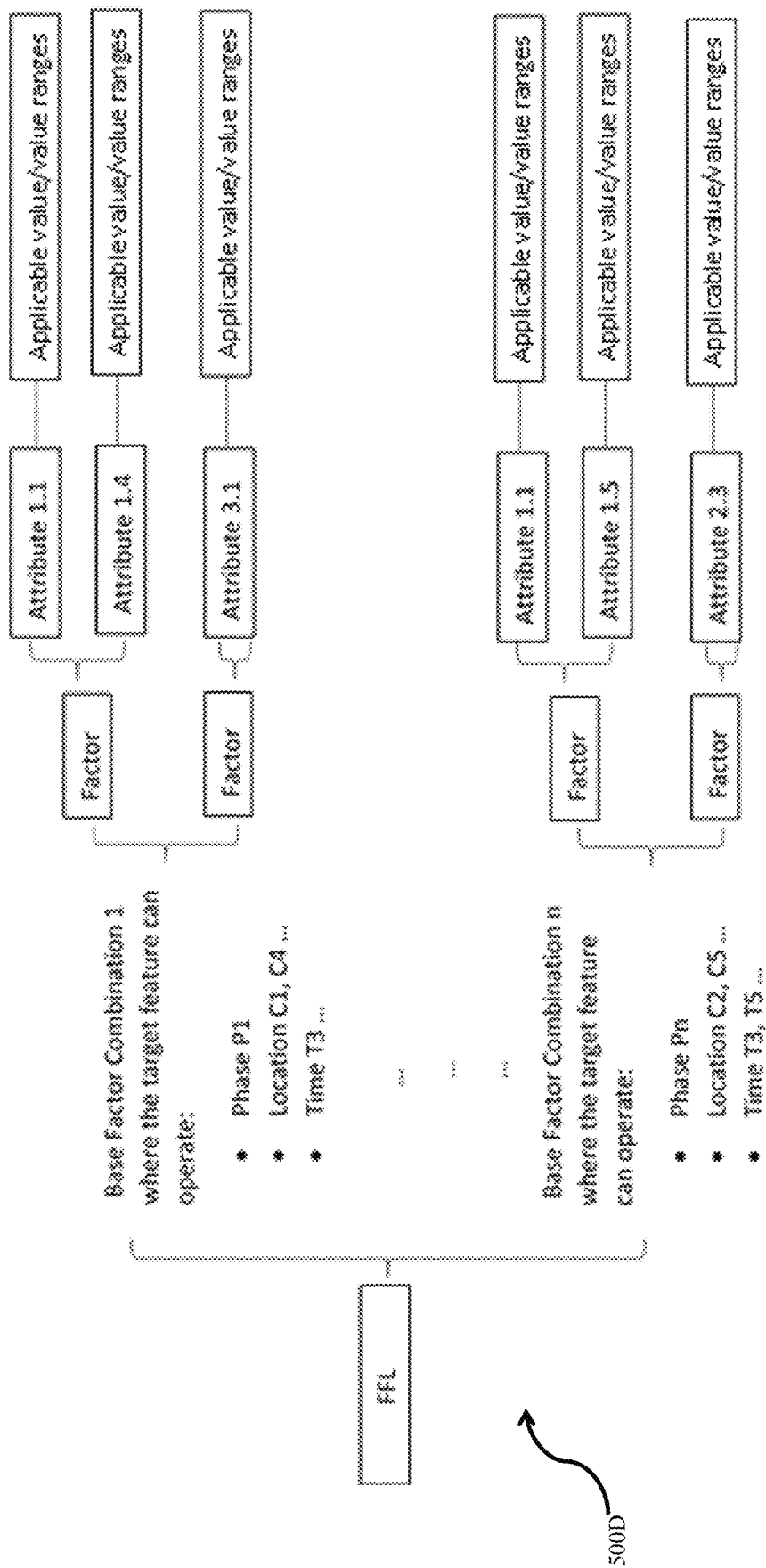
FIG. 5D illustrates a flow chart of structure of Final Factor List (FFL) for a subject software feature in accordance with at least one embodiment of the claimed subject matter.

FIG. 5B illustrates a flow chart 500B of IFL for a subject software feature to come up with FFL in accordance with at least one embodiment of the claimed subject matter. In an embodiment, for each IFL, one FFL is created. At step 1304, BSBLP-1's IFL is obtained from the applicable BSBLP list for the software feature, shown at step 1302. At step 1306, BSBLP-1's base factor values are identified where the target feature can operate. At step 1308, the BSBLP-1's IFL is obtained. At step 1310, elements in BSBLP-1's IFL based on the base factor values in the step 1306 is processed. The processed result is saved in a Final Factor List (FFL). At step 1312, the method determines whether any BSBLP is processed or not. In case, if the method determines any BSBLP is processed, the method proceeds to not processed BSBLP. The process is further described in conjunction with FIG. 5C. FIG. 5C illustrates a flow chart 500C of IFL for FFL in accordance with at least one embodiment of the claimed subject matter. At step 1402, a detail of BSBLP-1's IFL is shown. Then, in the next step 1404, non-base factor 1 attribute 1 is obtained. At step 1406, the method determines whether attribute 1 has at least one overlapping value for each base factor as shown in FIG. 5B step 1306. At step 1408, attribute and relevant values are added to the Final Factor List (FFL) for this IFL upon determining an affirmative response to step 1406. At step 1410, the method determines whether any IFL attribute is processed or not upon determining a negative response to step 1406. In case, any IFL attribute is processed, then the method proceeds to the next not processed IFL attribute. FIG. 5D illustrates a flow chart 500D of structure of Final Factor List (FFL) for a subject software feature in accordance with at least one embodiment of the claimed subject matter. For each of the base factor combination, the selected attributes are those with the same or overlapping base factor values with the software feature.

Figure 6A:
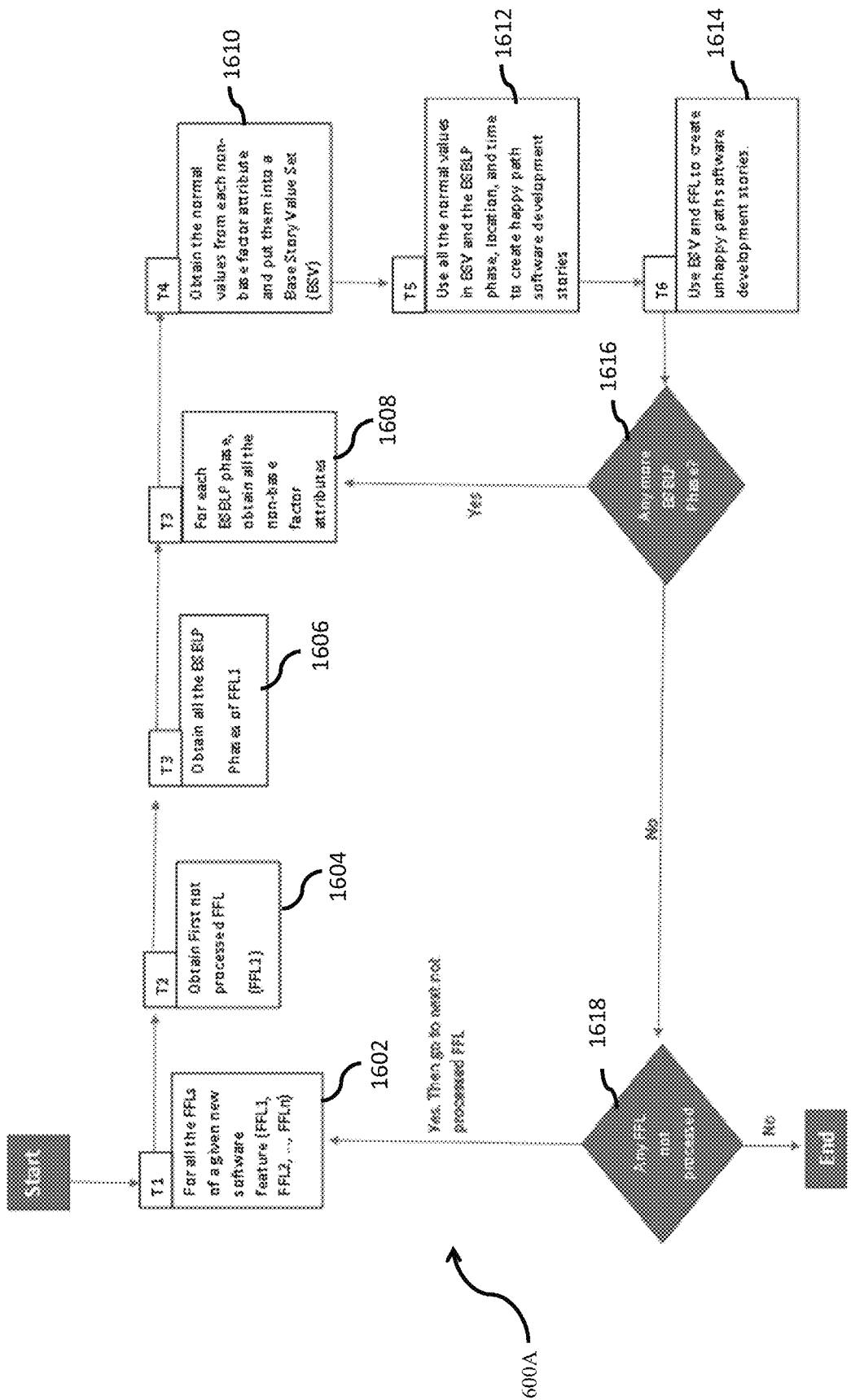
FIG. 6A illustrates a flow chart to create software development and testing stories in accordance with at least one embodiment of the claimed subject matter.

FIG. 6A illustrates a flow chart 600A to create software development and testing stories in accordance with at least one embodiment of the claimed subject matter. The step 1602 is for all the FFLs of a subject new software feature. At step 1604, the first not processed FFL (FFL1) is obtained. At step 1606, all the BSBLP phases of FFL1 are obtained. At step 1608, for each BSBLP phase, all the non-base factor attributes are obtained. At step 1610, the normal values from each non-base factor attributes are obtained and placed into a base story value set (BSV). At step 1612, all the normal values are used in BSV and BSBLP phase, location, and time to create happy path software development stories. At step 1614, BSV and FFL are used to create unhappy path software development stories. At step 1616, the method determines if there are any more BSBLP phase. In case, there is any more BSBLP phase, the method proceeds to perform step 1608. In case, any more BSBLP phase is not determined, then at step 1618, the method determines if any FFL is processed or not. If any FFL is processed, the method proceeds to the next not processed FFL.

Figure 6B:
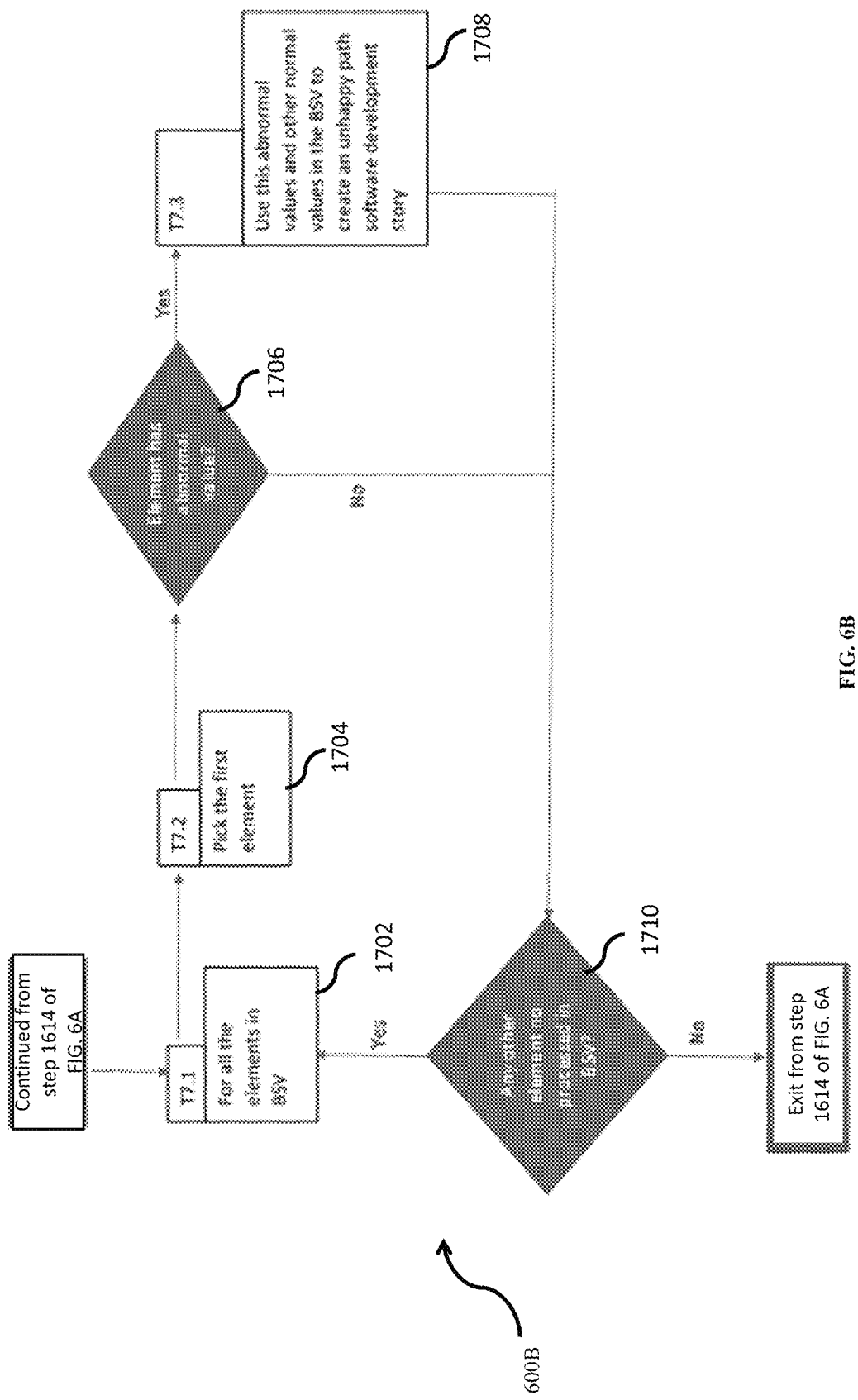
FIG. 6B illustrates a flow chart to create software development unhappy path stories in accordance with at least one embodiment of the claimed subject matter.

FIG. 6B illustrates a flow chart 600B to create software development unhappy path stories in accordance with at least one embodiment of the claimed subject matter. The step 1702 is for all the elements in BSV. At step 1704, the first element is picked. At step 1706, the method identifies whether the element has an abnormal value or not. At step 1708, upon identifying that the element has an abnormal value, the method uses these abnormal values and other normal values in the BSV to create an unhappy path software development story. At step 1710, the method determines if any other elements need to be processed in BSV. If any other elements need to be processed then the method restarts the step 1702.

The present specification further describes an example of the FIG. 6A and FIG. 6B, in the case of pacing BSBLP and its FFL. In an embodiment, there are three base factors are identified i) Phases (storage, set up, therapy, therapy off, and ending); ii) Location (surgery room, clinician office, patient's home, and airport); ii) Time (in 3 months scale starting from the device out of manufacturing till 10 years in the future). In an embodiment, there are two non-base factors are identified i) Battery as Hardware factor with the attributes and values shown above; ii) Software monitoring feature with the attributes and values shown above.

The new feature (heart failure prevention) will not be applicable for the storage phase, so it's not selected. The first applicable phase then is the setup phase. During this phase, the only applicable location is the surgery room. The time could be starting from a couple of weeks to 3 years (normally) with abnormal values of being more than 3 years. The battery state could be in a valid or an invalid state and battery percentage could be in either of the ranges defined above. The software monitoring feature usually is off in this phase.

With the information above (stored in FFL), the present system can generate happy path stories. During the setup phase in the surgery room, the device is out of manufacturing for 1 year, the battery is at 95% full and the monitoring feature is turned off, the physician can enable the new heart failure prevention feature in a duo-chamber pacing device. During the setup phase in the surgery room, the device is out of manufacturing for 2 years, the battery is at 85% full and the monitoring feature is turned off, can the physician enable the new heart failure prevention feature in a duo-chamber pacing device?

Further, the following unhappy path stories can be generated (which are usually questions): During the setup phase in the surgery room, the device is out of manufacturing for more than 3 years, the battery is at 85% full and the monitoring feature is turned off, can physician enable the new heart failure prevention feature in a duo-chamber pacing device? During the setup phase in the surgery room, the device is out of manufacturing for 2 years, the battery is at 79% full and the monitoring feature is turned off, can the physician enable the new heart failure prevention feature in a duo-chamber pacing device?

Figure 6C:
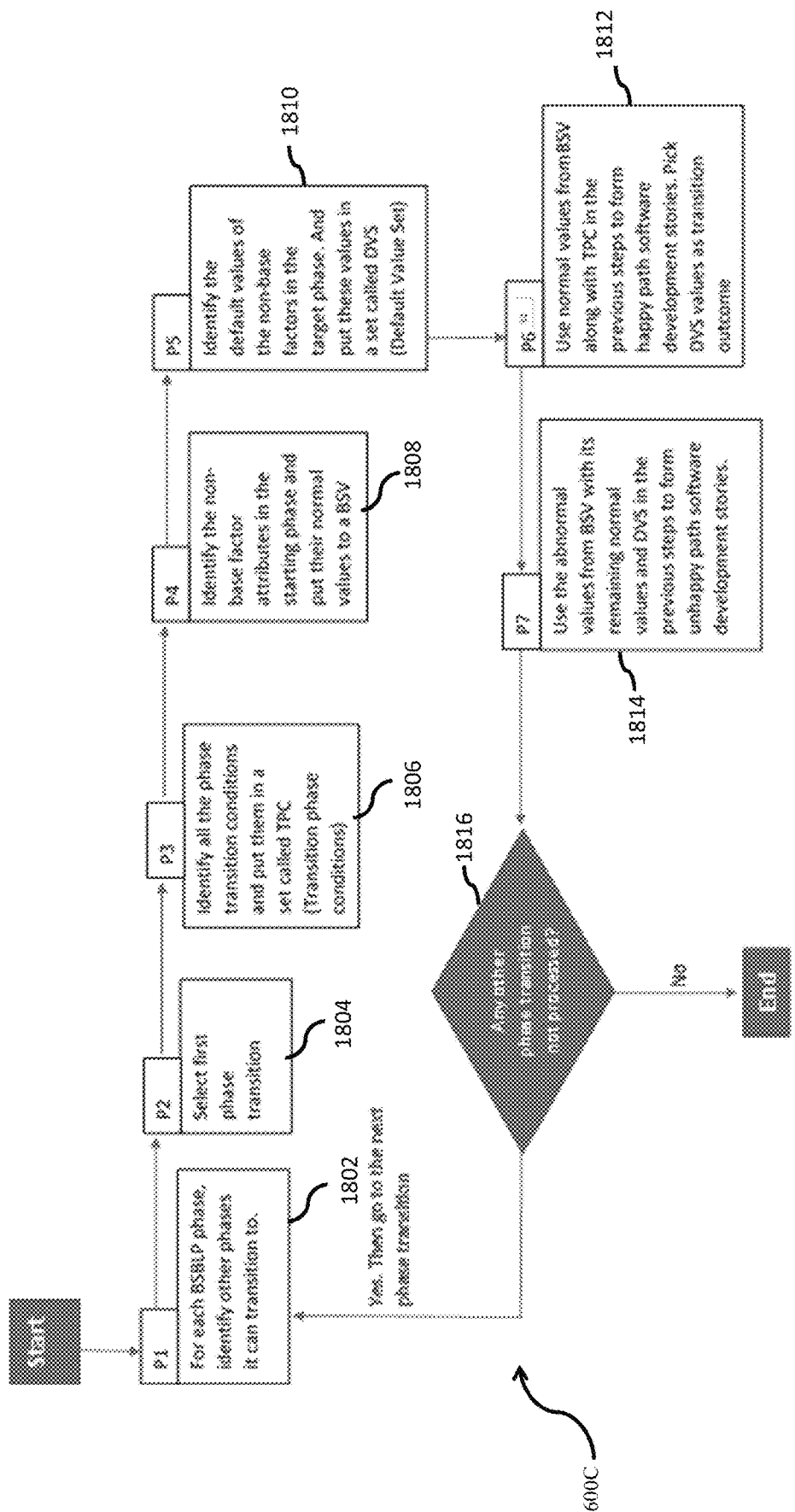
FIG. 6C illustrates a flow chart to create software development and testing stories for phase transition in accordance with at least one embodiment of the claimed subject matter.

FIG. 6C illustrates a flow chart 600C to create software development and testing stories for phase transition in accordance with at least one embodiment of the claimed subject matter. At step 1802, for each BSBLP phase, the method identifies other phases it can transition to. At step 1804, the first phase transition is selected. At step 1806, all the phase transition conditions are identified and put them in a set called TPC (Transition phase conditions). At step 1808, the non-base factor attributes in the starting phase are identified and put their normal values to a BSV. At step 1810, the default values of the non-base factor in the target phase are identified and put their values in a set called DVS (Default value set). At step 1812, the method uses normal values from BSV along with TPC in the previous steps to form happy path software development stories. Then the DVS values are picked as transition outcomes. At step 1814, the method uses the abnormal values from BSV along with its remaining normal values and DVS in the previous steps to form unhappy path software development stories. At step 1816, the method determines whether any other phase transition is processed or not. If any other phase transition is processed, then the method proceeds to the next phase transition.

In the case of pacing BSBLP, the treatment phase can transition back to set up phase; the treatment phase can transition to therapy off state; the treatment phase can transition to the near end of life phase; the treatment phase can (very unlikely) directly transition to the end of life phase. The present specification uses the example of a treatment phase transition to the near end of life phase. The condition is battery life is down to 6 months but more than 3 months.

Figure 6D:
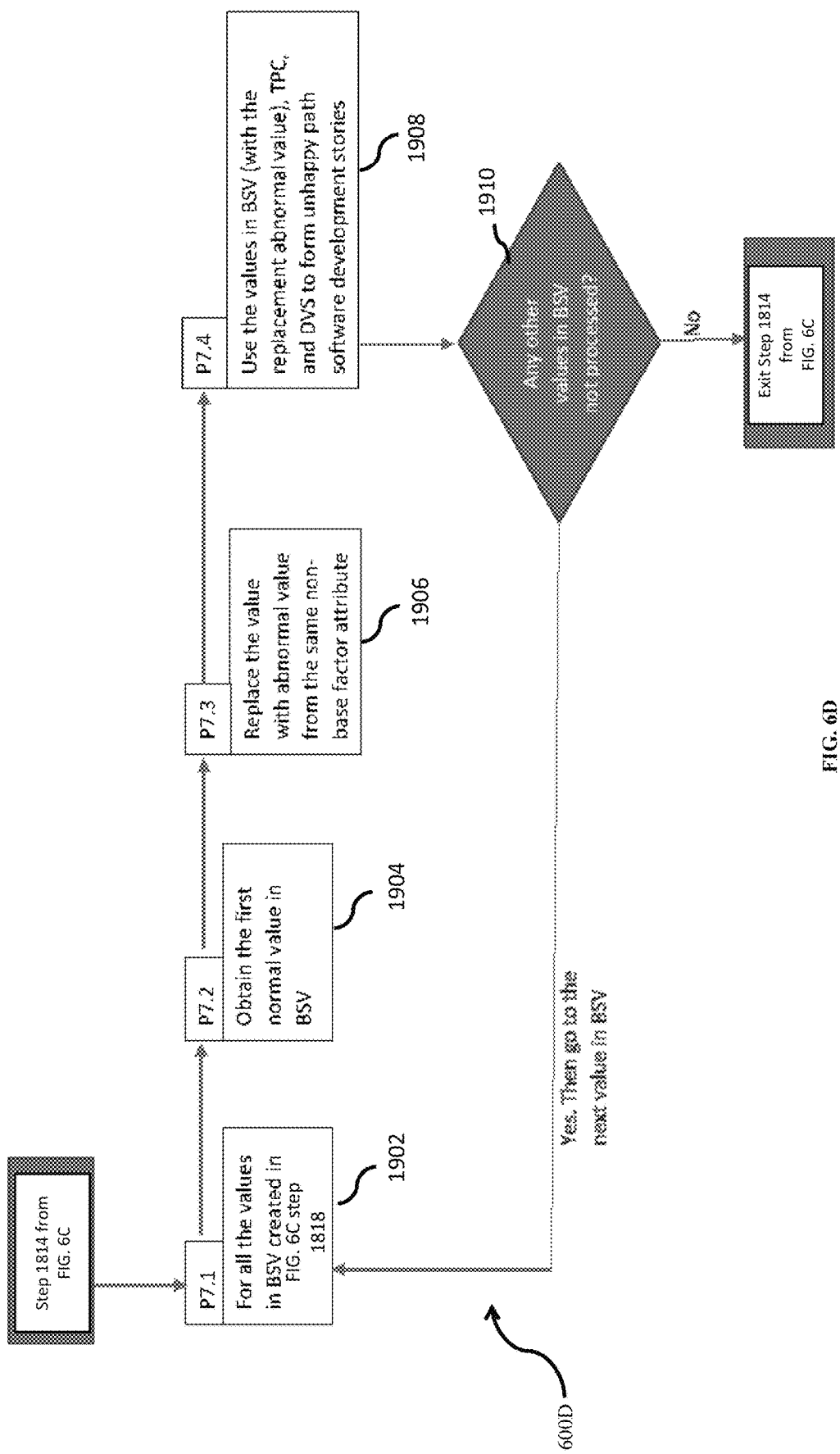
FIG. 6D illustrates a flow chart to create unhappy path software development and testing stories for phase transition in accordance with at least one embodiment of the claimed subject matter.

FIG. 6D illustrates a flow chart 600D to create unhappy path software development and testing stories for phase transition in accordance with at least one embodiment of the claimed subject matter. The step 1902 depicts, for all the values in BSV created in FIG. 6C step 1818. At step 1904, the first normal value in BSV is obtained. At step 1906, the value with the abnormal value from the same non-base factor attribute is replaced. At step 1908, the values are used in BSV (with the replacement of abnormal value), TPC, and DVS to form unhappy path software development stories. At step 1910, the method determines if any other values in BSV are processed or not. If there are any values processed, the method proceeds to the next value in BSV.

The present disclosure further provides an example in the case of pacing BSBLP phase transitions.

For happy path stories: When the device is in the patient's home and monitoring and pacing the patient's heart—if pacing device battery life remains at 3.1 months, the pacing device transition from pacing phase to the early end of life phase with the following default values after the transition: Monitoring feature being turned off; and the pacing mode will be "ramp up".

When the device is in the clinician office and monitoring and pacing the patient's heart, If pacing device battery life remains at 5 months, the pacing device transition from the pacing phase to the early end of life phase with the following default values after the transition: Monitoring feature being turned off; and the pacing mode will be "ramp up".

For unhappy path stories: When the device is in airport security checkpoint, and monitoring is off but still pacing— if the pacing device battery life remains at 5 months, can the pacing device transition from pacing phase to an early end of life phase with the following default values after the transition? i) Monitoring feature is turned off; and ii) the pacing mode will be "ramp up".

When the device is in the patient's home and monitoring and pacing the patient's heart, If pacing device battery life remains at 2.9 months, can the pacing device transition from the pacing phase to an early end of life phase with the following default values after the transition? i) Monitoring feature is turned off; and ii) The pacing mode will be "ramp up".

Thus the present system and method provide a computerized AI analytical model that utilizes the multi-dimensional knowledgebase (MDK) to automate the generation of comprehensive software development and testing stories. The present system and method create traceability for a plurality of design requirements and a plurality of regulation compliances. Further, the present system and method use artificial intelligence to reduce software design time, cost, and risk. Further, the present system and method improve the performance of a software system and related hardware which leads to higher user satisfaction and lower safety risks. The present system and method replace manual software designing to reduce defects and risk of product performance and market release. Furthermore, the present system and method minimize patients' safety risks caused by software defects.

Unless otherwise defined, all terms (including technical and scientific terms) used in this disclosure have the same meaning as commonly understood by one of ordinary skill in the art to which this disclosure belongs. It is to be understood that the phrases or terms used with the present inventive subject matter is for the purpose of description and not of limitation. As will be appreciated by one of skill in the art, the present disclosure may be embodied as a device, system, and method or computer program product. Further, the embodiments may take the form of a computer program product on a computer-readable storage medium having computer-usable program code embodied in the medium. The present systems, devices, and methods have been described above with reference to specific examples, however, other embodiments and examples than the above description are equally possible within the scope of the claimed subject matter. The scope of the disclosure may only be limited by the appended patent claims. Even though modifications and changes may be suggested by the persons skilled in the art, it is the intention of the inventors and applicants to embody within the patent warranted heron all the changes and modifications as reasonably and properly come within the scope of the contribution the inventors and applicants to the art. The scope of the embodiments of the inventive subject matter is ascertained with the claims as submitted at the time of filing the complete specification.

What is claimed is:

1. A system to generate a plurality of software development and testing stories for software related to a device, comprising:
   a design specification system containing software design data;
   a collection module to collect software design data from the design specification system;
   an identification module to identify a plurality of Base Software Business Logic Paths (BSBLP) comprising a plurality of base factors and a plurality of non-base factors, wherein the identification module identifies the base factors, the non-base factors, and a plurality of values of the base factors, and the non-base factors for each BSBLP;
   a creation module to place the base factors, the non-base factors, and the values of the base factors, and the non-base factors for each BSBLP inside an Initial Factor List (IFL) to build one or more Multi-Dimensional Knowledgebases (MDK);
   a selection module to select a plurality of relevant BSBLP from the MDK for a subject software feature to be analyzed;
   an analysis module to utilize the relevant BSBLP selected by the selection module to perform a factor impact analysis on the subject software feature by processing the IFL for the relevant BSBLPs to develop a Final Factor List (FFL),
   wherein the FFL containing a list of a plurality of applicable non-base factors for the subject software feature;
   a development module to generate the software development and testing stories by utilizing the FFL; and
   a feeding module to feed the software development and testing stories back to a user computing device;

a software configured to control the device or view data of the device;

wherein each BSBLP is a multi-dimensional space defined by the base factors and the non-base factors, within a BSBLP all base factors are applicable for each non-base factors such that the space defined by all the base factors move in one unit in the space defined by the non-base factors;

wherein the software generates software design data based on data of the device;

wherein the system generates software development and testing stories based on the software design data and transmits the software development and testing stories back to the software.

2. The system as claimed in claim 1, wherein the base factors comprising: a time base factor, a location base factor, and a plurality of phase base factors.

3. The system as claimed in claim 1, wherein the non-base factors comprising: a hardware non-base factor, a user non-base factor, a plurality of existing software features, an external non-base factor, an environmental non-base factor.

4. The system as claimed in claim 1, wherein each of the MDK consists of the BSBLP, each BSBLP is independent and cannot be concurrently run with any other BSBLP.

5. The system as claimed in claim 1, wherein each of the BSBLP is a multi-dimensional space defined by the base factors and the non-base factors, within a BSBLP all base factors are applicable for each non-base factor such that the space defined by all the base factors move in one unit in the space defined by the non-base factors;

wherein the base factors comprising: a time base factor, a location base factor, and a plurality of phase base factor;

wherein the non-base factors comprising: a hardware non-base factor, a user non-base factor, a plurality of existing software features, an external non-base factor, an environmental non-base factor.

6. The system as claimed in claim 5,
each of the MDK consists of the BSBLP, each BSBLP is independent and cannot be concurrently run with any other BSBLP.

7. The system of claim 6, wherein the various non-base factors include corresponding factor attributes, wherein each of the factor attributes including one or more of a plurality of normal values, a plurality of abnormal values, and a plurality of default values.

8. The system of claim 7, wherein the FFL comprising a plurality of elements, wherein, for each element in the FFL, one or more possible element values are analyzed, wherein each BSBLP comprising a phase and phase transition, and for each BSBLP phase and phase transition, the software develop stories are created for the subject software feature by using the FFL.

9. A computer-implemented method, executed by a processor operatively connected to a memory, for generating a plurality of software development and testing stories, wherein the computer-implemented methods employ AI model for generating software development and testing stories for software related to a device, comprising:
collecting software design data from a design specification system through a collection module,
wherein the design specification system containing the software design data, comprising using a software configured to control the device or view data of the device to generate software design data based on data of the device;

identifying a plurality of Base Software Business Logic Paths (BSBLP) through an identification module, wherein the Base Software Business Logic Paths comprising a plurality of base factors and a plurality of non-base factors, wherein the identification module identifies the base factors, the non-base factors, and a plurality of values of the base factors, and the non-base factors for each BSBLP;

placing, by a creation module, the base factors, the non-base factors, and the values of the base factors, and the non-base factors for each BSBLP inside an Initial Factor List (IFL) to build one or more Multi-Dimensional Knowledgebases (MDK);

selecting, by a selection module, a plurality of relevant BSBLP from the MDK for a subject software feature to be analyzed;

performing, by an analysis module, a factor impact analysis on the subject software feature by processing the IFL for the relevant BSBLPs to develop a Final Factor List (FFL), wherein the FFL containing a list of a plurality of applicable non-base factors for the subject software feature;

generating, by a development module, the software development, and testing stories by utilizing the FFL, comprising generating software development and testing stories based on the software design data generated by the software; and transmitting the software development and testing stories back to the software;

feeding, by a feeding module, the software development, and testing stories back to a user computing device;

wherein each of the plurality of BSBLP is a multi-dimensional space defined by the base factors and the non-base factors, within a BSBLP all base factors are applicable for each non-base factors such that the space defined by all the base factors move in one unit in the space defined by the non-base factors.

10. The computer-implemented method as claimed in claim 9, wherein the base factors comprising: a time base factor, a location base factor, and a plurality of phase base factors.

11. The computer-implemented method as claimed in claim 9, wherein the non-base factors comprising: a hardware non-base factor, a user non-base factor, a plurality of existing software features, an external non-base factor, an environmental non-base factor.

12. The computer-implemented method as claimed in claim 9, wherein each of the MDK consists of the BSBLP, each BSBLP is independent and cannot be concurrently run with any other BSBLP.

13. The computer-implemented method as claimed in claim 9, wherein each of the BSBLP is a multi-dimensional space defined by the base factors and the non-base factors, within a BSBLP all base factors are applicable for each non-base factors such that the space defined by all the base factors move in one unit in the space defined by the non-base factors;

wherein the base factors comprising: a time base factor, a location base factor, and a plurality of phase base factor;

wherein the non-base factors comprising: a hardware non-base factor, a user non-base factor, a plurality of existing software features, an external non-base factor, an environmental non-base factor.

14. The computer-implemented method as claimed in claim 13, wherein each of the MDK consists of the BSBLP, each BSBLP is independent and cannot be concurrently run with any other BSBLP.

15. The method of claim 14, wherein the various non-base factors include corresponding factor attributes, wherein each of the factor attributes including one or more of a plurality of normal values, a plurality of abnormal values, and a plurality of default values.

16. The method of claim 15, wherein the FFL comprising a plurality of elements, wherein, for each element in the FFL, one or more possible element values are analyzed, wherein each BSBLP comprising a phase and phase transition, and for each BSBLP phase and phase transition, the software develop stories are created for the subject software feature by using the FFL.

* * * * *